(12) United States Patent
Schubert et al.

(10) Patent No.: US 7,531,669 B2
(45) Date of Patent: May 12, 2009

(54) METHODS FOR TREATING NEURAL DISORDERS AND CONDITIONS, AND COMPOUNDS USEFUL THEREFOR

(75) Inventors: David R. Schubert, La Jolla, CA (US); Yuanbin Liu, San Diego, CA (US); Thomas Baiga, San Marcos, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 26 days.

(21) Appl. No.: 11/323,987

(22) Filed: Dec. 30, 2005

(65) Prior Publication Data

US 2006/0160812 A1 Jul. 20, 2006

Related U.S. Application Data

(63) Continuation-in-part of application No. PCT/US2004/021399, filed on Jul. 2, 2004.

(60) Provisional application No. 60/484,942, filed on Jul. 3, 2003.

(51) Int. Cl.
*C07D 231/10* (2006.01)
*C07D 231/12* (2006.01)
(52) U.S. Cl. ............... 548/375.1; 548/376.1; 548/377.1
(58) Field of Classification Search ............... 548/375.1, 548/376.1, 377.1
See application file for complete search history.

(56) References Cited

U.S. PATENT DOCUMENTS 4,945,021 A * 7/1990 Takata et al. .................. 430/76

OTHER PUBLICATIONS

Shim et al., "Hydrazinocurcumin, a Novel Synthetic Curcumin Derivative, Is a Potent Inhibitor of Endothelia Cell Proliferation", Bioorganic & Medicinal Chemistry 10 (2002) 2439-2444.*
Hcaplus 112:76878.*
Dorwald F. A. Side Reactions in Organic Synthesis, 2005, Wiley: VCH, Weinheim p. IX of Preface.*
Caplus English Abstract AN 1910:3479 Auwers et al. 1910.*
Caplus English abstract 1976, AN 1977:497777 Leonov V.P.*
Caplus Abstract AN 1906:63756 Japp Francis et al.*
Khazaei and Vaghei, Microwave assisted facile cleavage of 2,4-Dinitrophenyl-hydrazones to their corresponding carbonyl compounds with N,N'-Dibromo-N,N'-1,2-ethanediylbis(p-toluenesulphonamide). Molecules, 7:717-720, 2002.
Hoaplus Database on STN, Chemical Abstracts Service, North America, Document No. 65:90671 (Sues et al., Organic photoconductive materials for electrophotography. Abstract US 3257203, Sep. 21, 1966.
Hoaplus Database on STN, Chemical Abstracts Service, North America, Document No. 138:98186 (Takahashi et al., Chemically-amplified negative-working resist compositions for processing with electron beam or X-ray. Abstract JP 2003005356, Oct. 8, 2003.

(Continued)

*Primary Examiner*—Rita J Desai
(74) *Attorney, Agent, or Firm*—Foley & Lardner LLP; Stephen E. Reiter

(57) ABSTRACT

In accordance with the present invention, there are provided novel compounds that protect neurons and/or promote neuroregeneration and/or promote memory formation. Such compounds are useful for treatment of a variety of neural disorders and conditions. In another aspect of the present invention, there are also provided formulations containing one or more of the above-described compounds, optionally further containing additional neurologically active compound(s) and/or adjuvants to facilitate delivery thereof across the blood/brain barrier. In still another aspect of the present invention, there are further provided methods for treating a wide variety of neurological indications, e.g., acute neural injuries, chronic injuries, promoting memory formation, and the like.

21 Claims, 20 Drawing Sheets

OTHER PUBLICATIONS

Hoaplus Database on STN, Chemical Abstracts Service, North America, Document No. 136:254351 (Nakatsuka et al., Organic electroluminescent devices containing diphenylthiophine derivative. Abstract JP 2002075648, Mar. 15, 2002.).

Hoaplus Database on STN, Chemical Abstracts Service, North America, Document No. 109:83352 (Takahashi et al, High sensitivity electrophotographic photoreceptor containing diphenyltriazole derivative as charge-transporting material. Abstract JP 63013049, Jan. 20, 1988.).

Hoaplus Database on STN, Chemical Abstracts Service, North America, Document No. 75:151564 (Eberle et al., Sedative phenylhydrazides. Abstract DE 2107238, Sep. 16, 1971.).

Hoaplus Database on STN, Chemical Abstracts Service, North America, Document No. 127:293249 (Bull et al., Preparation of quinoxalinediones as NMDA receptor antagonists. Abstract WO 9732873, Sep. 12, 1997).

International Search Report for PCT Application No. PCT/US2004/21399.

* cited by examiner

General procedure for Pyrazole formation:

regioisomers when $R^1$ does not = $R^2$

US 7,531,669 B2

METHODS FOR TREATING NEURAL DISORDERS AND CONDITIONS, AND COMPOUNDS USEFUL THEREFOR

RELATED APPLICATIONS

This application is a continuation-in-part of international application no. PCT/US2004/021399, filed Jul. 2, 2004, which claims priority from U.S. provisional application No. 60/484,942, filed Jul. 3, 2003, the entire contents of each of which are hereby incorporated by reference herein.

GOVERNMENT ACKNOWLEDGEMENT

This invention was made with United States government support under Grant Nos. NS-10279 (Liu), NS-09658 (Schubert) and NS-28121 (Schubert) from the National Institutes of Health. The United States Government may have certain rights in this invention.

FIELD OF THE INVENTION

The present invention relates to novel compounds which are useful for the treatment of a variety of neural disorders and conditions. In a particular aspect, the present invention relates to methods for the treatment of neural disorders and conditions employing invention compounds. In a further aspect, the present invention relates to methods for protecting neurons in a subject in need thereof. In still another aspect, the present invention relates to methods for promoting neuroregeneration in a subject in need thereof. In yet another aspect, the present invention relates to methods for promoting memory formation in a subject in need thereof.

BACKGROUND OF THE INVENTION

There are currently no effective treatments for acute neural injuries (such as stroke and spinal cord injury) and chronic neurodegenerative diseases (such as Alzheimer's disease, Parkinson's disease, Huntington's disease, amytrophical lateral sclerosis, retinal degeneration, etc.). Drugs that can protect neurons and/or promote neuroregeneration are urgently needed to treat these devastating injuries or diseases, as well as promote memory formation.

Neurotrophic growth factors (including nerve growth factor, brain-derived neurotrophic factor, neurotrophin-3 and -4/5, ciliary neurotrophic factor, glial cell-derived neurotrophic factor, and fibroblast growth factor) have emerged in the past decade as promising drug candidates for treating acute and chronic neurodegenerative diseases. These protein neurotrophic growth factors play an essential role in the maintenance of neuronal populations from development through adulthood. However, clinical studies with these protein-based neurotrophic factors have proved to be disappointing due to their poor pharmacokinetic behavior, low bioavailability, inability to penetrate the brain, and pleiotropic effects. Therefore, much effort has been invested in the search for non-peptidyl small neurotrophic molecules.

Additional targets of interest include CaM Kinase II, which is involved in memory formation.

Small neurotrophic molecules have the potential to be administered orally and to successfully traverse the blood/brain barrier. Numerous companies around the world have invested heavily in this area for many years and screened tens of thousands of compounds. Unfortunately, however, no compounds have been identified thus far which are promising enough to go to clinical trials (for reviews of this field, see Thoenen and Sendtner, Nat. Neurosci. Supplement 5, 1046-1050 (2002); Saragovi and Gehring, Trends Pharmacol. Sci. 21, 93-98 (2000); Xie and Longo, Prog. Brain Res. 128, 333-347 (2000)).

An abnormal rate of apoptosis may be responsible for at least some of the neuronal cell death in neurodegenerative diseases such as Alzheimer's disease and Parkinson's disease (Thompson, Science 267, 1456-1462 (1995)). Inhibitors of the apoptosis pathway therefore can be used to promote neuronal survival. Peptide-based inhibitors of caspases, key enzymes in the apoptosis pathway, will suffer from the same drawback as neurotrophins in terms of their ability to cross the blood-brain barrier. Small molecule inhibitors of the apoptosis pathway are still in the early exploratory stage (for review, see Huang, Chem. & Biol. 9, 1059-1072 (2002)).

Accordingly, there is still a need in the art for compounds that can protect neurons and/or promote neuroregeneration and/or promote memory formation. Such compounds will be useful for treatment of a variety of neural disorders and conditions.

SUMMARY OF THE INVENTION

In accordance with the present invention, there are provided novel compounds that protect neurons and/or promote neuroregeneration and/or promote memory formation. Such compounds are useful for treatment of a variety of neural disorders and conditions.

In accordance with another aspect of the present invention, there are also provided formulations containing one or more of the above-described compounds, optionally further containing additional neurologically active compound(s) and/or adjuvants to facilitate delivery thereof across the blood/brain barrier.

In still another aspect of the present invention, there are further provided methods for treating a wide variety of neurological indications, e.g., acute neural injuries, chronic injuries, promoting memory formation, and the like.

DETAILED DESCRIPTION OF THE INVENTION

Figure 1:
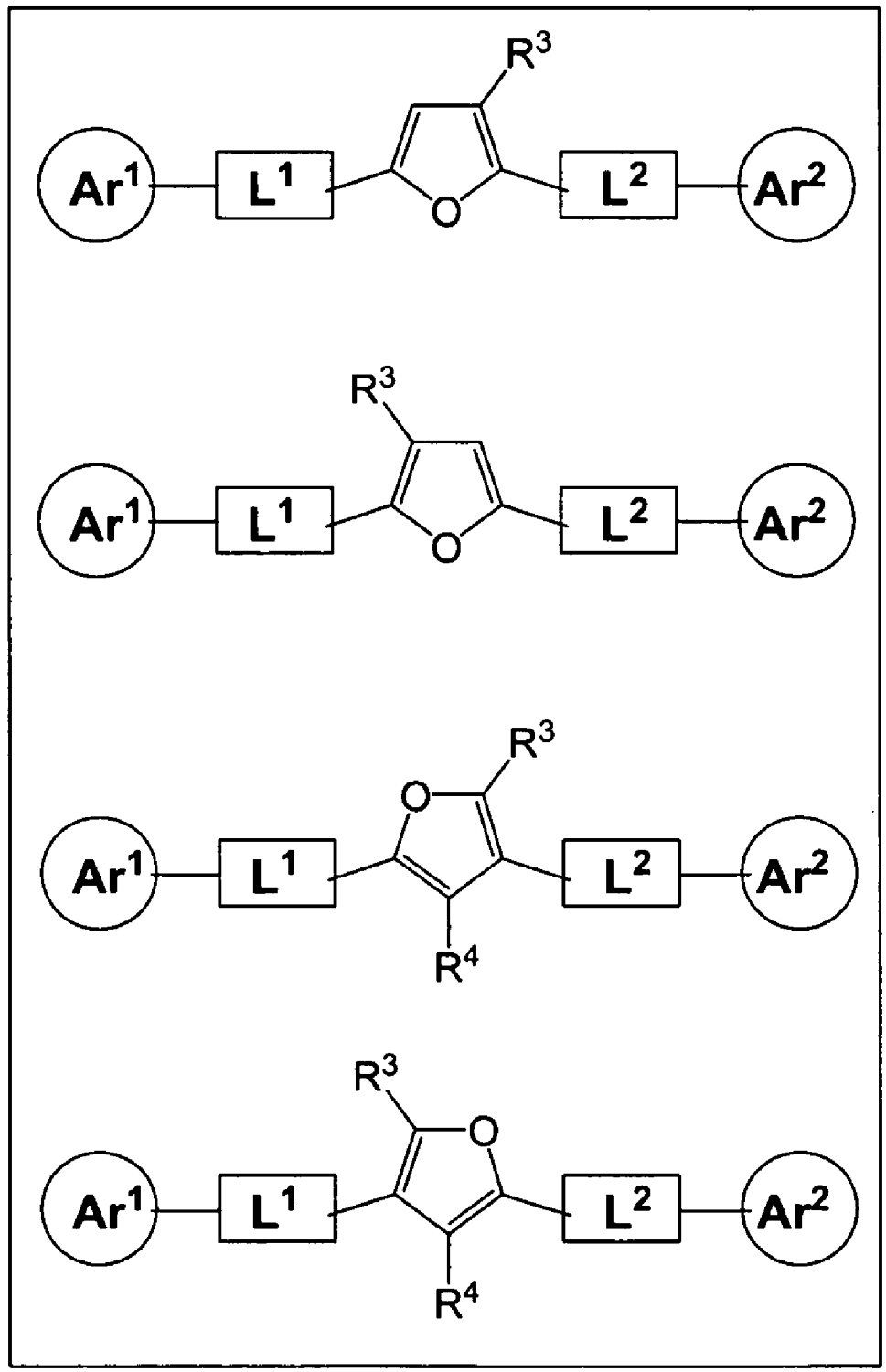
FIG. 1 illustrates several possible substitution patterns for invention compounds having a furan core ring.
Figure 2:
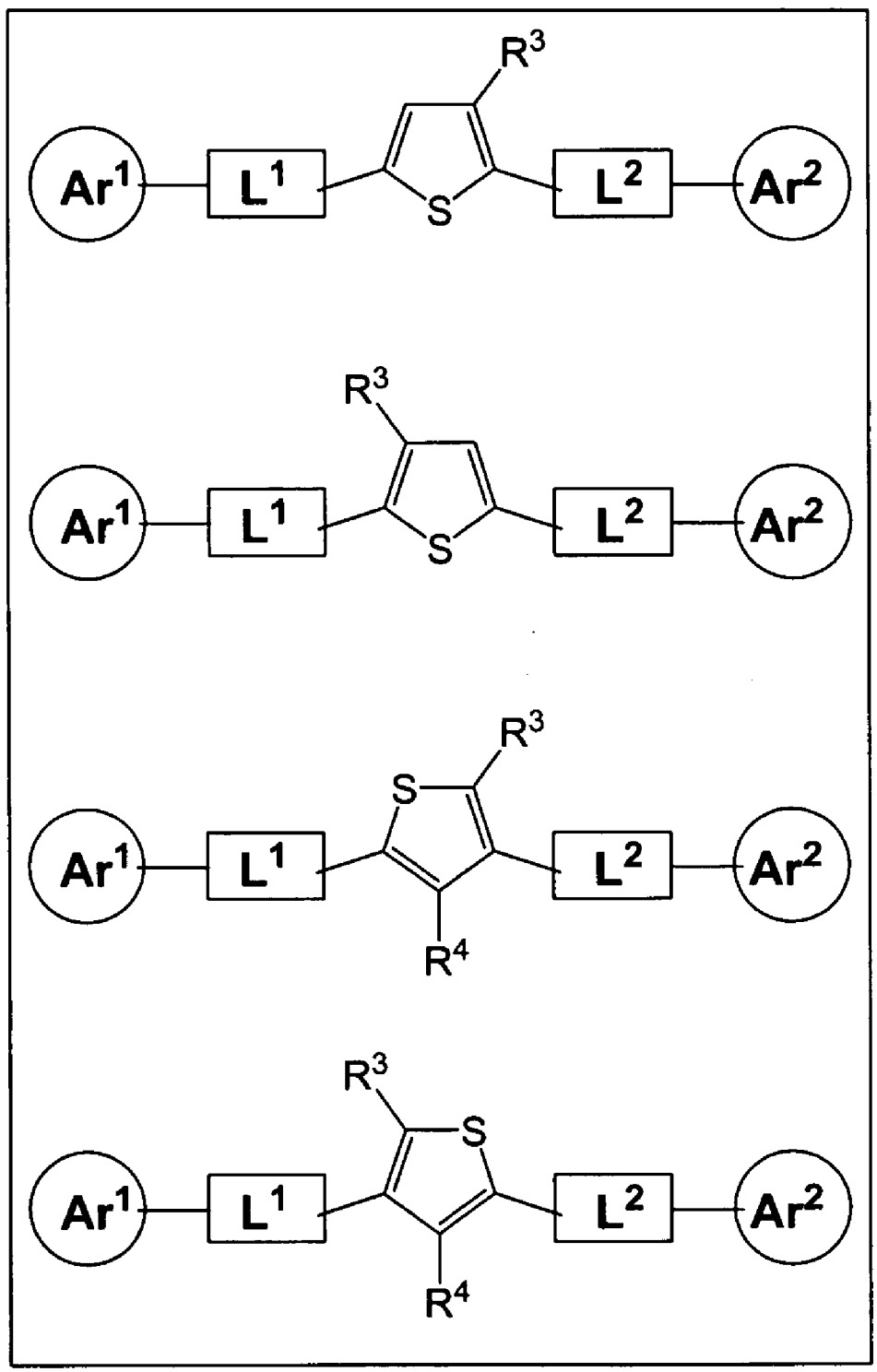
FIG. 2 illustrates several possible substitution patterns for invention compounds having a thiophene core ring.
Figure 3:
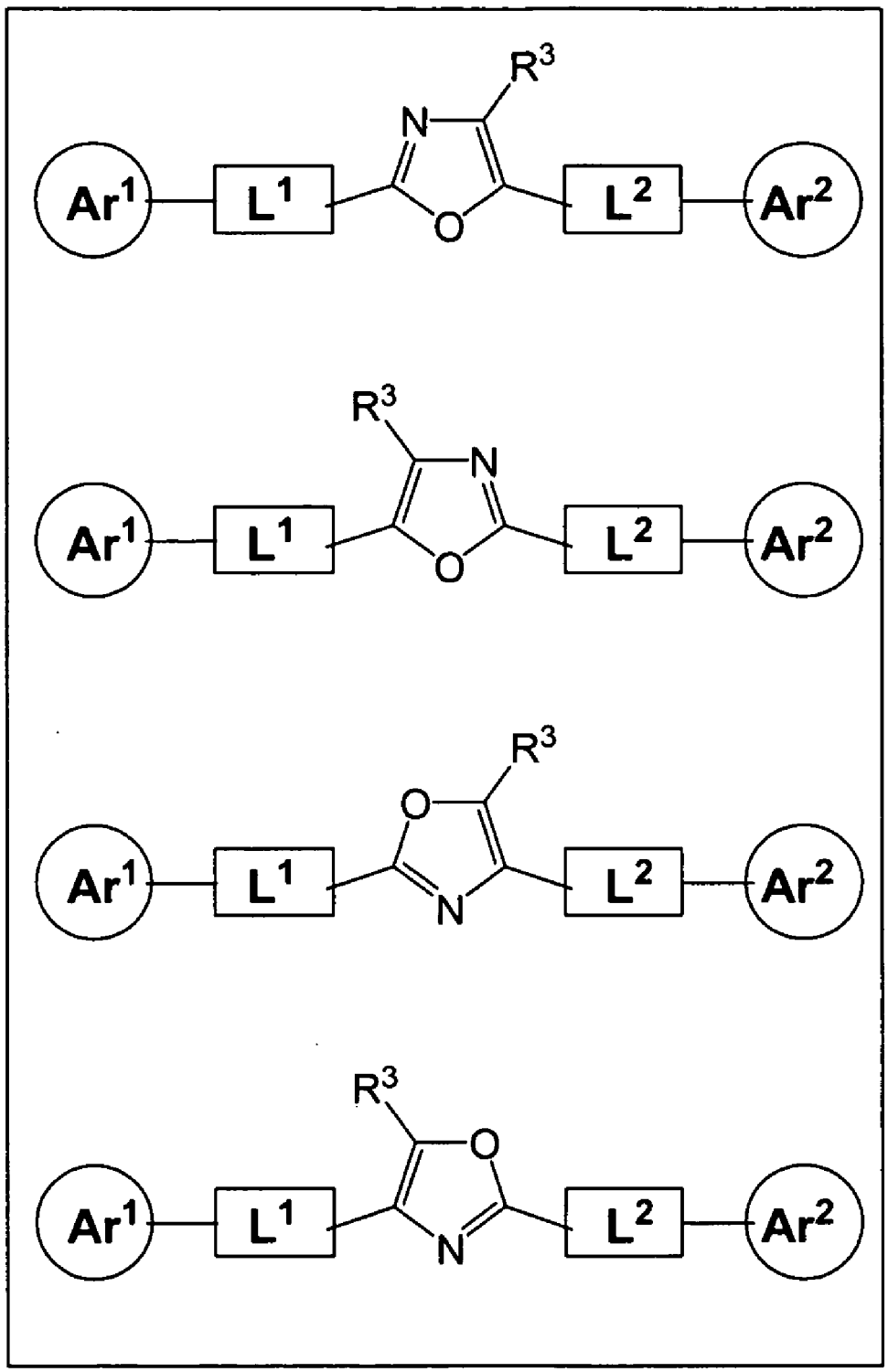
FIG. 3 illustrates several possible substitution patterns for invention compounds having an oxazole core ring.
Figure 4:
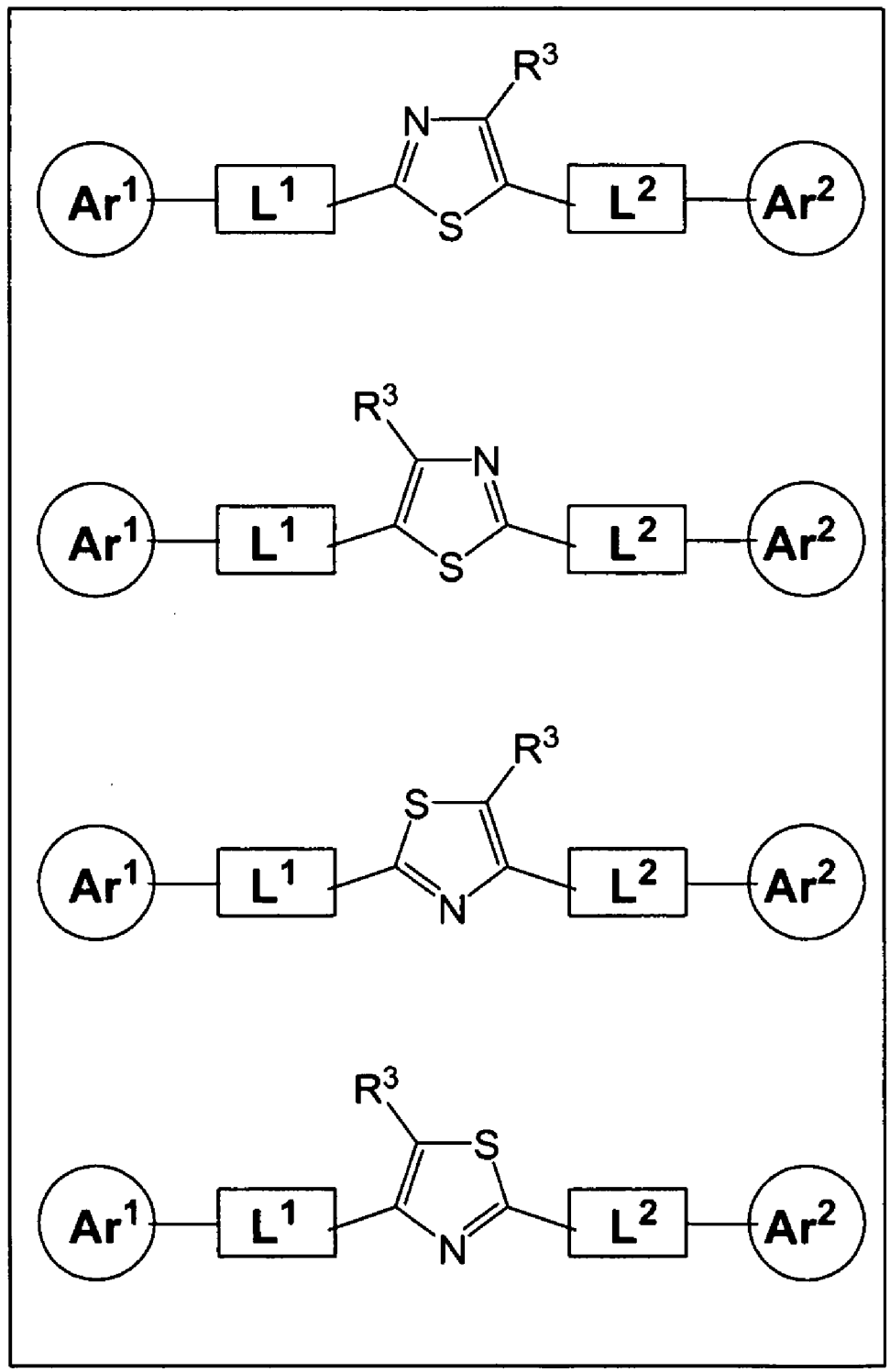
FIG. 4 illustrates several possible substitution patterns for invention compounds having a thiazole core ring.
Figure 5:
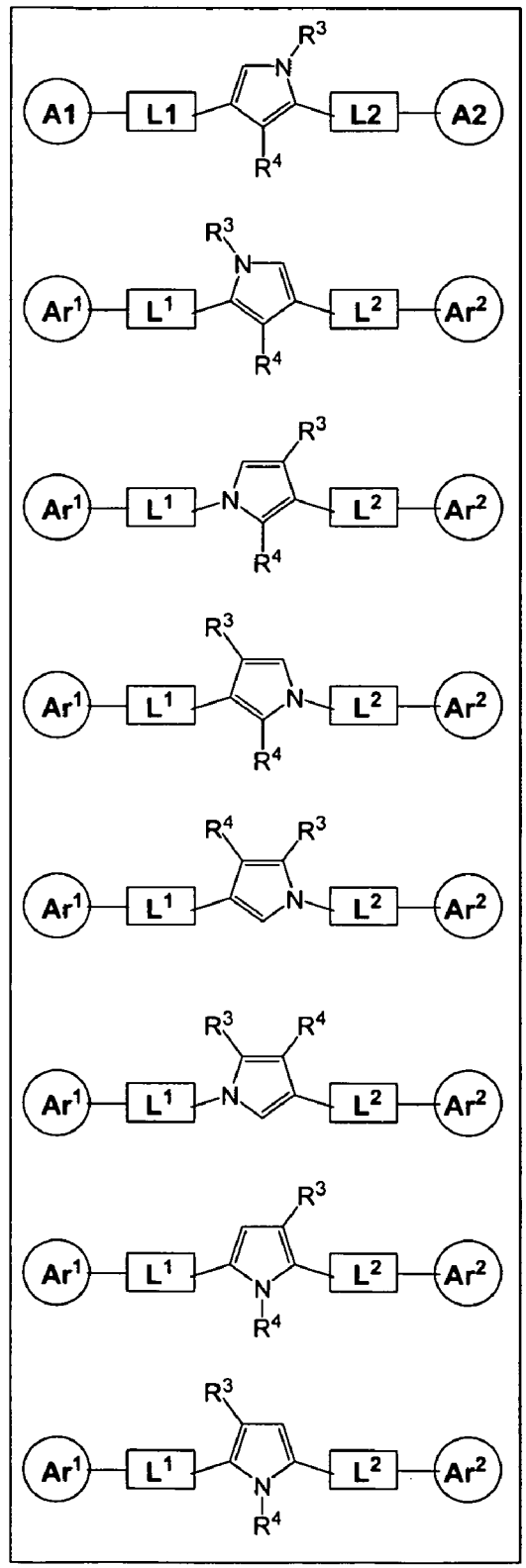
FIG. 5 illustrates several possible substitution patterns for invention compounds having a pyrrole core ring.
Figure 6:
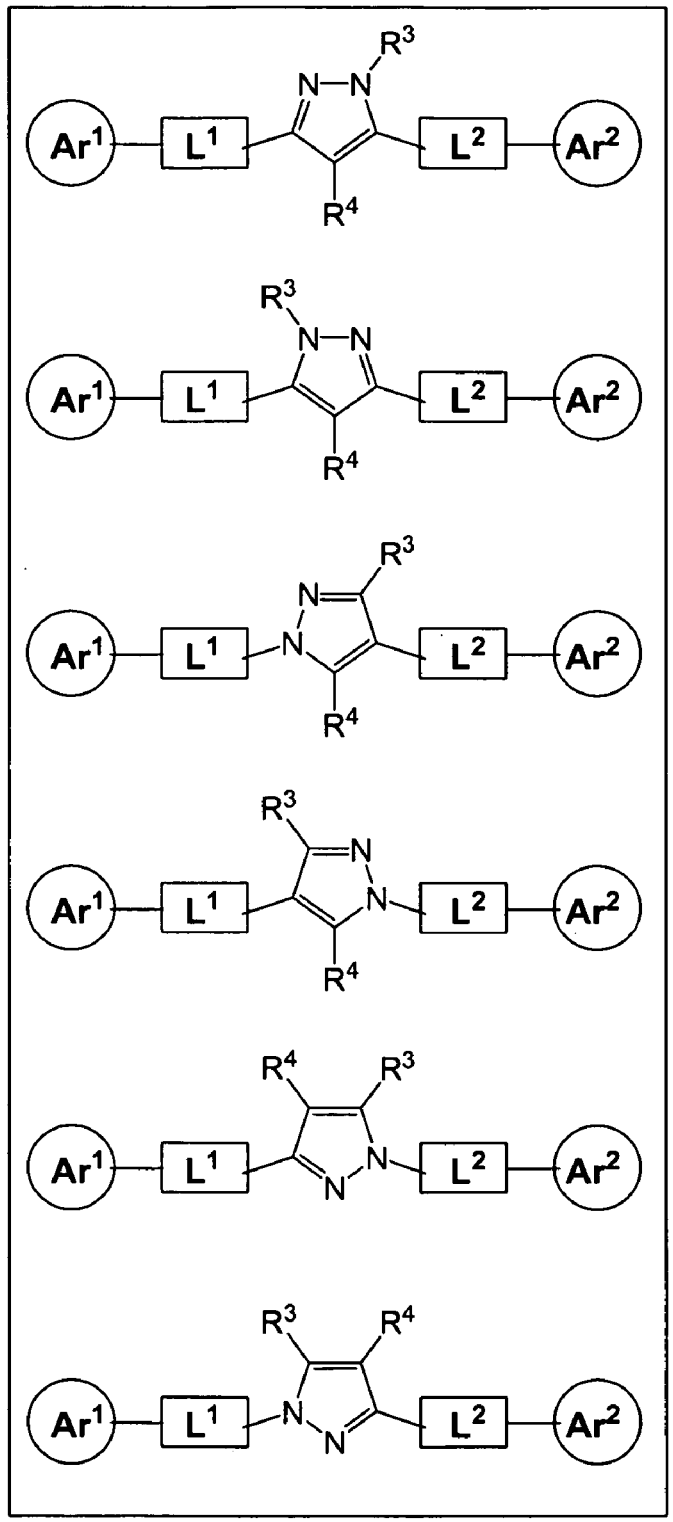
FIG. 6 illustrates several possible substitution patterns for invention compounds having a pyrazole core ring.
Figure 7:
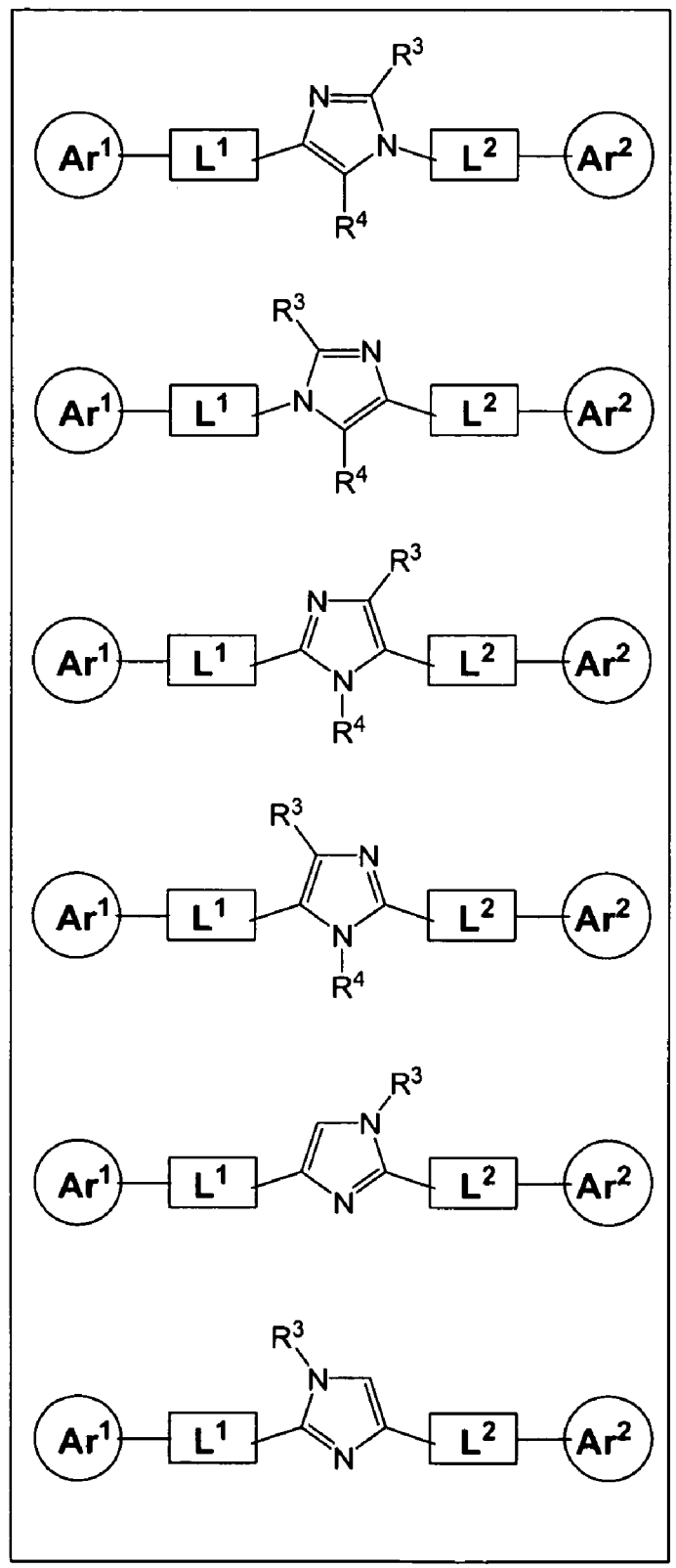
FIG. 7 illustrates several possible substitution patterns for invention compounds having an imidazole core ring.
Figure 8:
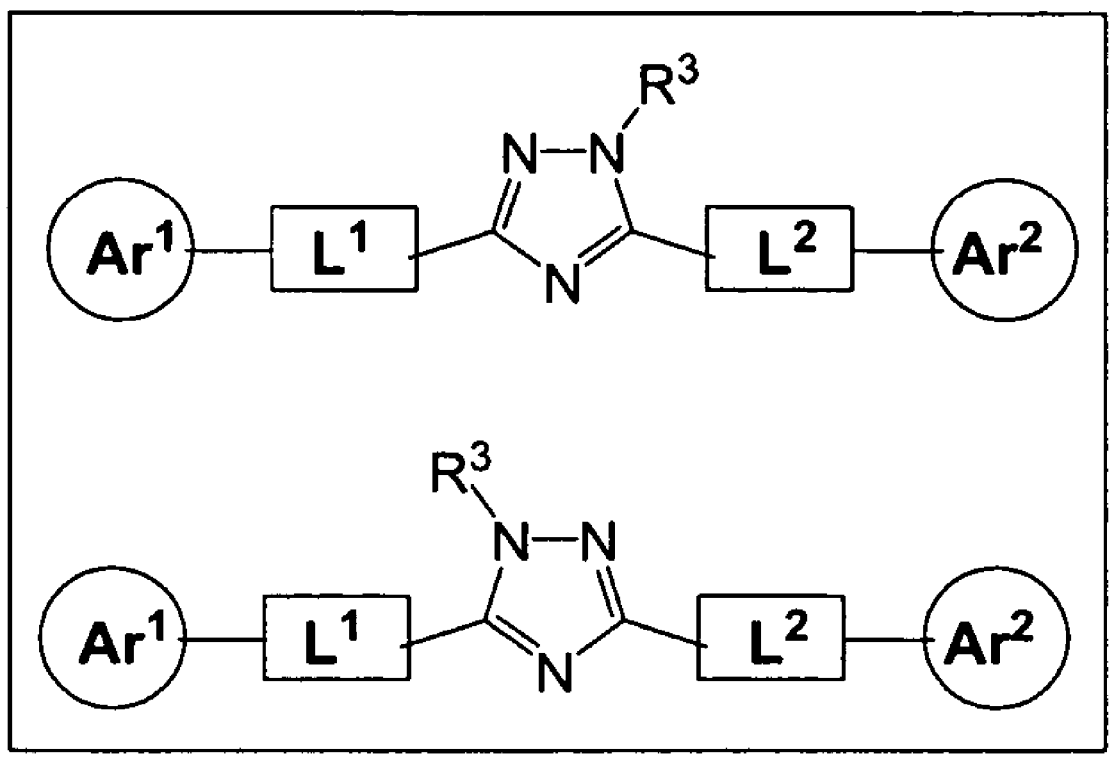
FIG. 8 illustrates several possible substitution patterns for invention compounds having a 1,2,4-triazole core ring.
Figure 9:
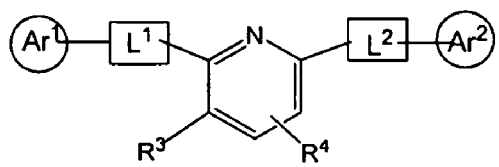
FIG. 9 illustrates several possible substitution patterns for invention compounds having a pyridine core ring.
Figure 9:
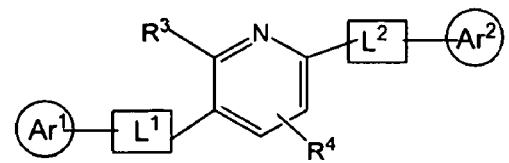
Figure 9:
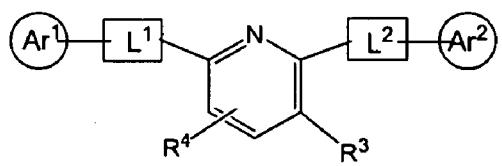
Figure 9:
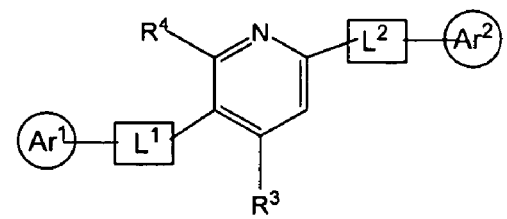
Figure 9:
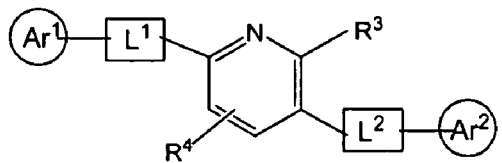
Figure 9:
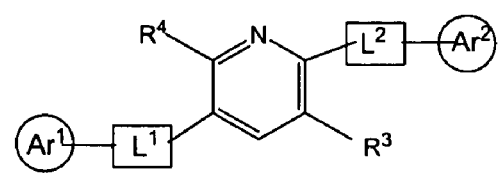
Figure 9:
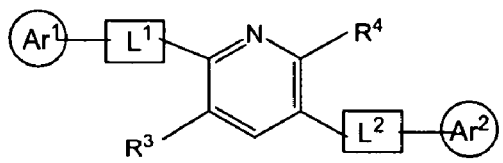
Figure 9:
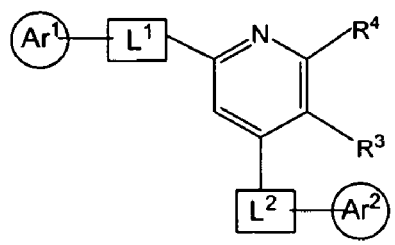
Figure 9:
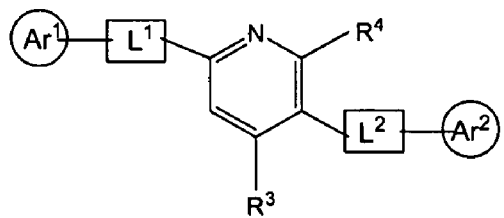
Figure 9:
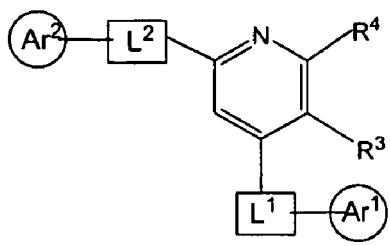
Figure 10:
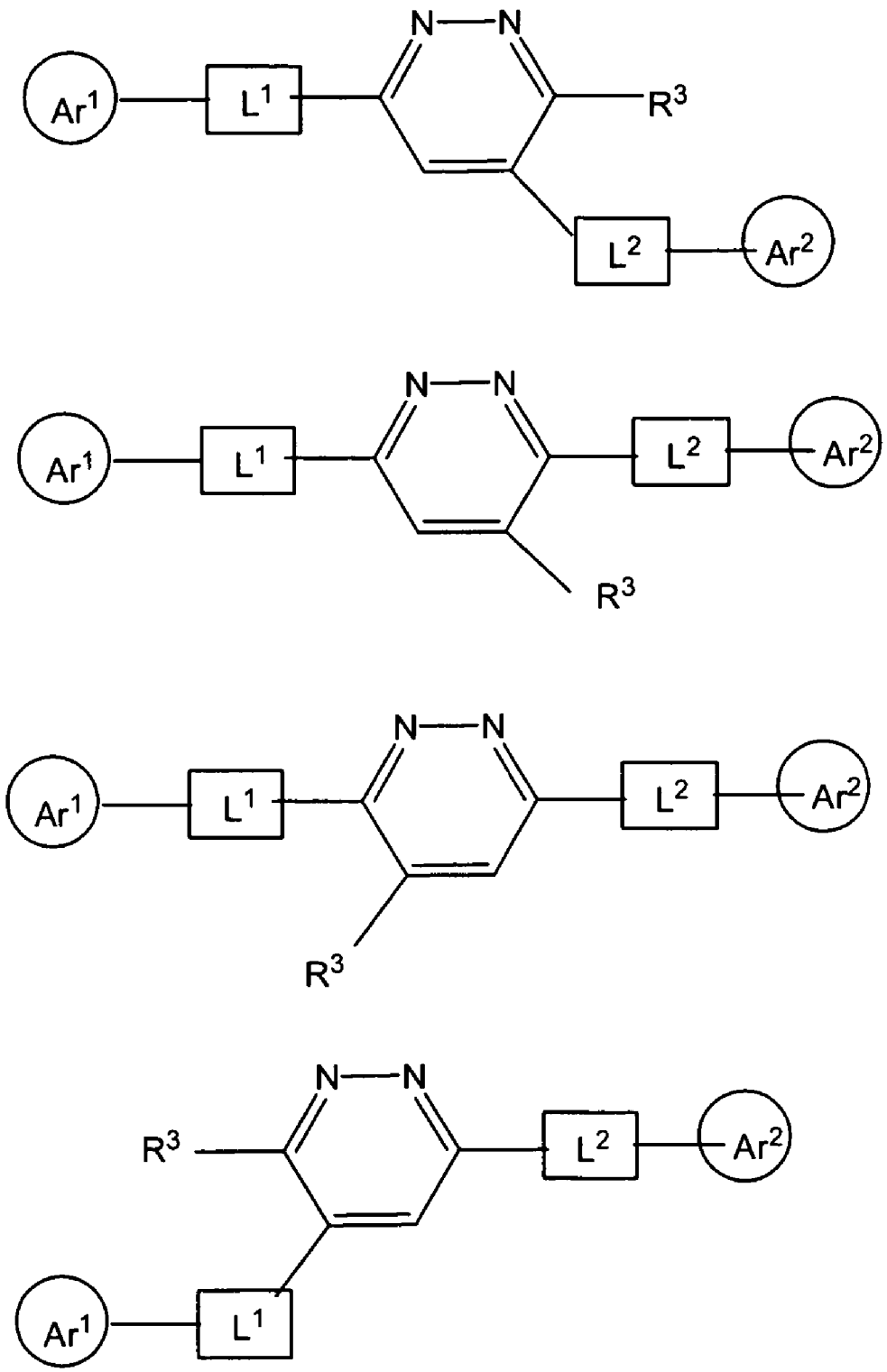
FIG. 10 illustrates several possible substitution patterns for invention compounds having a pyridazine core ring.
Figure 11:
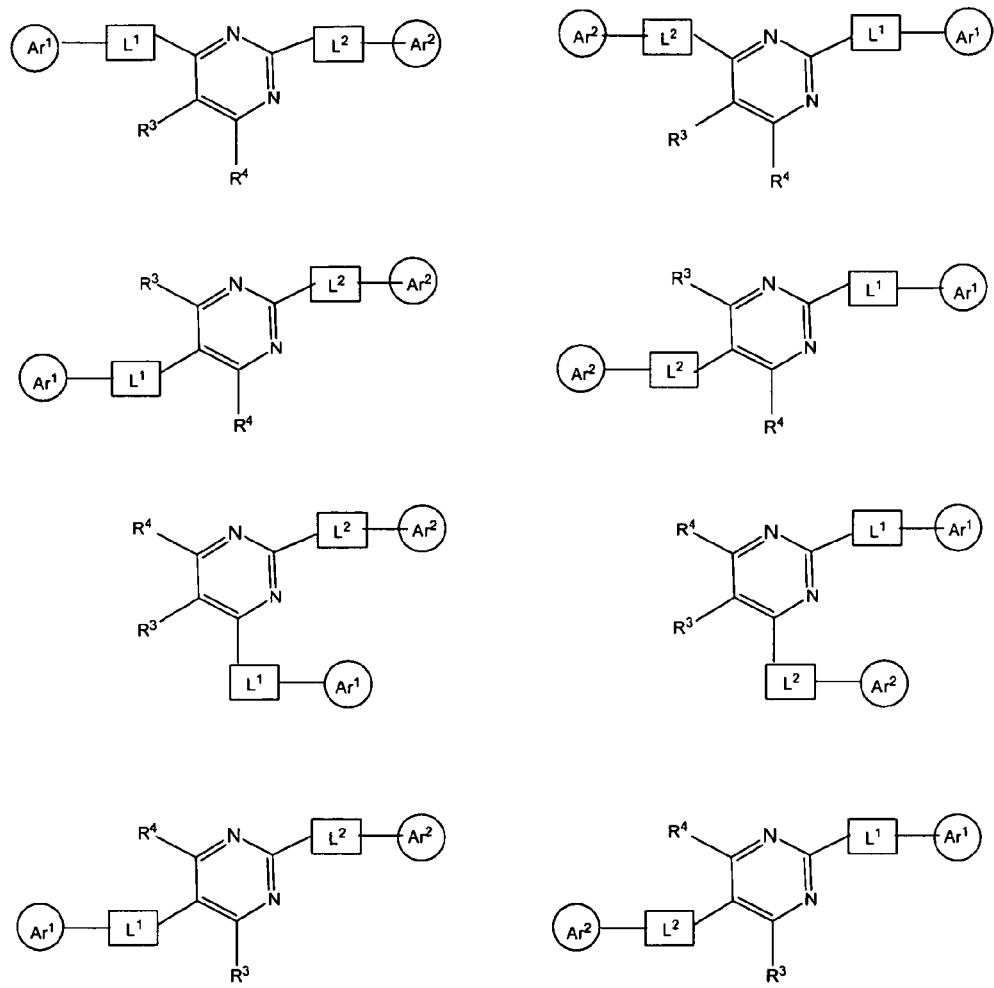
FIG. 11 illustrates several possible substitution patterns for invention compounds having a pyrimidine core ring.
Figure 12:
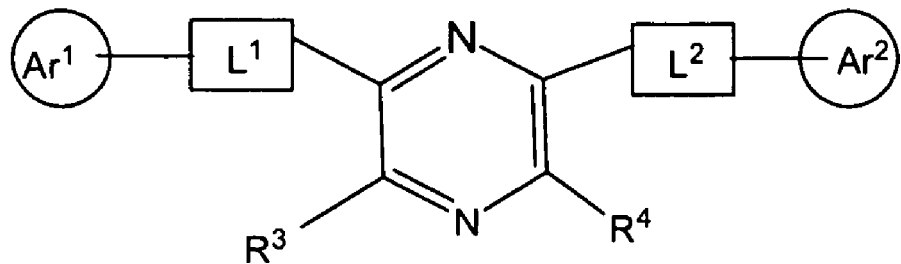
FIG. 12 illustrates several possible substitution patterns for invention compounds having a pyrazine core ring.
Figure 12:
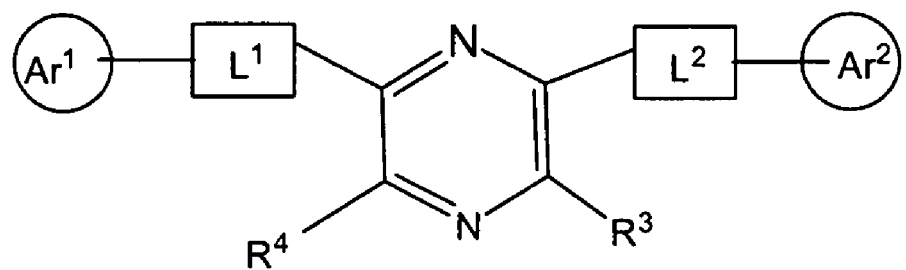
Figure 12:
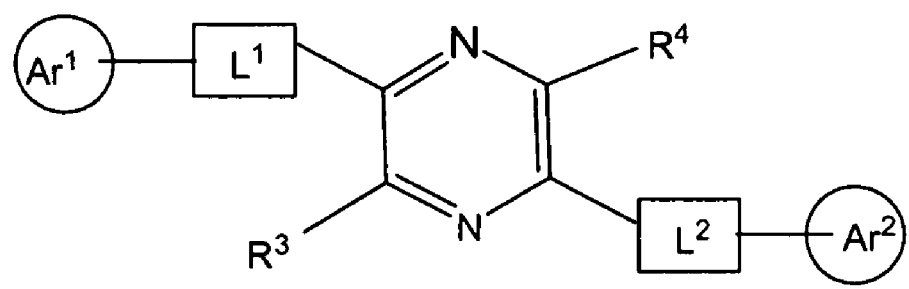
Figure 12:
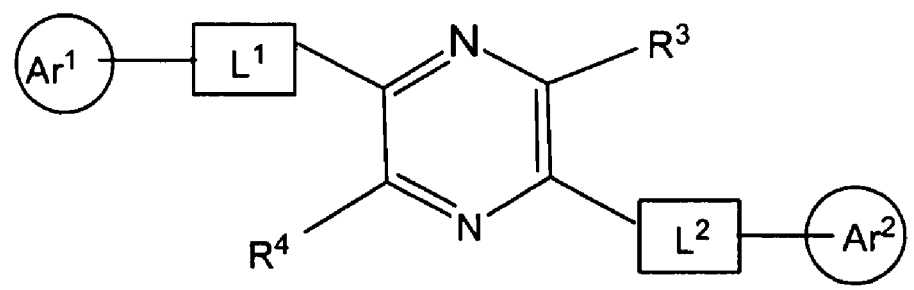

In accordance with the present invention, there are provided compounds comprising Formula (I) as follows:

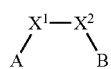

(I)

wherein:
A is =CHR, —CH$_2$R, or —C(=O)R and B is H; or
A and B are joined to form an aromatic ring wherein A is (CR)$_n$ and B is (CR)$_m$—X$^4$;
X$^1$ is O, S, N or NR,
X$^2$ and X$^4$ are independently O, S, N, NR, or CR, provided, however, that only one of X$^1$, X$^2$ and X$^4$ is O or S,
m is 1 or 2, and
n is 1 or 2, provided, however, that the sum of m+n is no greater than 3,
any one R is -L$^1$-Ar$^1$,
any one R is -L$^2$-Ar$^2$,
any one R is —R$^3$, and
any remaining R groups are R$^4$, provided, however, that the -L$^1$-Ar$^1$, -L$^2$-Ar$^2$, and —R$^3$ moieties, in any order, define a 1,2,4-substitution pattern about the central ring,
L$^1$ and L$^2$ are independently a covalent bond or a linker having a 1-4 atom backbone,
Ar$^1$ and Ar$^2$ are independently optionally substituted aryl or heteroaryl moieties,
R$^3$ is an optionally substituted branched alkyl, cycloalkyl, aryl, aralkyl, heteroaryl or heteroarylalkyl moiety, and
R$^4$ is H or optionally substituted alkyl, aryl, aralkyl, heteroaryl or heteroarylalkyl.

Embodiments of the invention include compounds of Formula (I) corresponding to Formula (II) as follows:

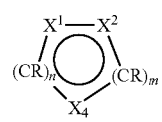

(II)

As indicated above, X$^1$ can be a heteroatom selected from O, S, N or NR. When the core ring of invention compounds is a 5-membered ring, and X$^1$ is nitrogen, the nitrogen atom will also carry a substituent thereon, in addition to the other ring atoms to which it is linked. When the core ring of invention compounds is a 6-membered ring, the valence of the nitrogen atom will be fully satisfied by the ring atoms to which it is linked, therefore, the nitrogen atom will bear no further substituents thereon.

X$^2$ and X$^4$ of invention compounds are independently selected from O, S, N or CR, provided, however, that only one of X$^1$, X$^2$ and X$^4$ is O or S. Thus, only one sulfur atom, or one oxygen atom is contemplated to be present in the core ring of invention compounds.

As reflected in Formula (II) set forth above, both 5- and 6-membered heterocyclic ring structures are contemplated as the core ring of invention compounds. Thus, compounds wherein m is 1 or 2, and compounds wherein n is 1 or 2; are contemplated. The sum of m and n, however, is no greater than 3, so that the core ring can accommodate 5 or 6 atoms, at least one of which is a heteroatom. For example, when m and n are both 1, the resulting compound will have a 5-membered ring core. Alternatively, when m is 1 and n is 2, or m is 2 and n is 1, the resulting compound will have a 6-membered ring core, with the choice of values for m and n controlling the location of X$^4$ on the ring.

As readily recognized by those of skill in the art, numerous 5- and 6-membered rings are contemplated by the present invention, for example, when m and n are both 1, X$^1$ is O, and X$^2$ and X$^4$ are each CR, the resulting ring is furan; when m and n are both 1, X$^1$ is S, and X$^2$ and X$^4$ are each CR, the resulting ring is thiophene; when m and n are both 1, X$^1$ is O, X$^2$ is CR, and X$^4$ is N, the resulting ring is oxazole; when m and n are both 1, X$^1$ is S, X$^2$ is CR, and X$^4$ is N, the resulting ring is thiazole; when m and n are both 1, X$^1$ is NR, and X$^2$ and X$^4$ are each CR, the resulting ring is pyrrole; when m and n are both 1, X$^1$ is NR, X$^2$ is N, and X$^4$ is CR, the resulting ring is pyrazole; when m and n are both 1, X$^1$ is NR, and X$^2$ is CR, and X$^4$ is N, the resulting ring is imidazole; when m and n are both 1, X$^1$ is NR, and X$^2$ and X$^4$ are each N, the resulting ring is 1,2,4-triazole.

Similarly, when m is 1 and n is 2, or m is 2 and n is 1, X$^1$ is N, and X$^2$ and X$^4$ are each CR, the resulting ring is pyridine; when m is 1 and n is 2, or m is 2 and n is 1, X$^1$ and X$^2$ are each N and X$^4$ is CR, the resulting ring is pyridazine; when m is 2 and n is 1, X$^1$ and X$^4$ are each N and each X$^2$ is CR, the resulting ring is pyrimidine (1,3-N); when m is 1 and n is 2, X$^1$ and X$^4$ are N and X$^4$ is CR, the resulting ring is pyrazine; and the like.

As reflected by Formula (II) set forth above, the core ring of invention compounds contains several R substituents. In accordance with the present invention, there are at least 3 different substituents present on the core ring, oriented about the ring in such a way as to define a 1,2,4-substitution pattern about the core ring. The minimal substituents contemplated include -L$^1$-Ar$^1$, -L$^1$-Ar$^2$, and —R$^3$. Thus, invention compounds include those compounds defined by Formula (II) above, wherein:
any one R is -L$^1$-Ar$^1$,
any one R is -L$^2$-Ar$^2$, and
any one R is —R$^3$.

When additional R groups are present on the core ring of invention compounds, any remaining R groups are R$^4$.

Ar$^1$ and Ar$^2$ are independently optionally substituted aryl or heteroaryl moieties, wherein "aryl", as used herein, refers to aromatic groups having in the range of 6 up to about 14 carbon atoms, and "substituted aryl" refers to aryl radicals further bearing one or more substituents selected from alkyl, substituted alkyl, cycloalkyl, substituted cycloalkyl, hydroxyl, alkoxy, aryloxy, mercapto, thioalkyl, thioaryl, carbonyl, aryl, substituted aryl, heterocyclic, substituted heterocyclic, halogen, trifluoromethyl, pentafluoroethyl, cyano, cyanomethyl, nitro, amino, amido, amidino, carboxyl, carboxamide, carbamate, ester, $SO_2X$, wherein X is H, R, $NH_2$, NHR or $NR_2$; $SO_3Y$, wherein Y is H, $NH_2$, NHR or $NR_2$; C(O)Z, wherein Z is OH, OR, $NH_2$, NHR or $NR_2$, and the like.

As used herein, "aralkyl" refers to an alkyl group as defined above substituted by an aryl group as defined above, and "substituted aralkyl" refers to aralkyl radicals further bearing one or more substituents selected from alkyl, substituted alkyl, cycloalkyl, substituted cycloalkyl, as well as any of the substituents set forth herein. Thus, aralkyl groups include benzyl, diphenylmethyl, and 1-phenylethyl (—$CH(C_6H_5)$ ($CH_3$)) among others.

As used herein, "heterocyclic" refers to cyclic (i.e., ring-containing) groups containing one or more heteroatoms (e.g., N, O, S, or the like) as part of the ring structure, and having in the range of 1 up to about 14 carbon atoms, and "substituted heterocyclic" refers to heterocyclic radicals further bearing one or more substituents as set forth above. Exemplary heterocyclic moieties include saturated rings, unsaturated rings, and aromatic heteroatom-containing ring systems, e.g., epoxy, tetrahydrofuran, oxazoline, pyrrole, pyridine, furan, and the like.

As used herein, "halogen" refers to fluoride, chloride, bromide or iodide radicals.

As used herein, "amino" refers to unsubstituted, monosubstituted and disubstituted amino groups, including the substituent —$NH_2$, "monoalkylamino," which refers to a substituent of the structure —NHR, wherein R is alkyl or substituted alkyl as set forth above, and "dialkylamino," which refers to a substituent of the structure —$NR_2$, wherein each R is independently alkyl or substituted alkyl as set forth above.

As employed herein, reference to "an amide group" embraces substituents of the structure —C(O)—$NR_2$, wherein each R is independently H, alkyl, substituted alkyl, aryl or substituted aryl as set forth above. When each R is H, the substituent is also referred to as "carbamoyl" (i.e., a substituent having the structure —C(O)—$NH_2$). When only one of the R groups is H, the substituent is also referred to as "monoalkylcarbamoyl" (i.e., a substituent having the structure —C(O)—NHR, wherein R is alkyl or substituted alkyl as set forth above) or "arylcarbamoyl" (i.e., a substituent having the structure —C(O)—NH(aryl), wherein aryl is as defined above, including substituted aryl). When neither of the R groups are H, the substituent is also referred to as "di-alkyl-carbamoyl" (i.e., a substituent having the structure —C(O)—$NR_2$, wherein each R is independently alkyl or substituted alkyl as set forth above).

As employed herein, reference to "a carbamate group" embraces substituents of the structure —O—C(O)—$NR_2$, wherein each R is independently H, alkyl, substituted alkyl, aryl or substituted aryl as set forth above.

As used herein, "heteroaryl" refers to aromatic groups containing one or more heteroatoms (e.g., N, O, S, or the like) as part of the aromatic ring, typically having in the range of 2 up to about 14 carbon atoms, and "substituted heteroaryl" refers to heteroaryl radicals further bearing one or more substituents selected from alkyl, substituted alkyl, cycloalkyl, substituted cycloalkyl, as well as any of the substituents set forth above.

As used herein, "heteroarylalkyl" refers to an alkyl groups, as defined above, substituted by one or more heteroaryl groups, as defined above, and "substituted heteroarylalkyl" refers to heteroarylalkyl radicals further bearing one or more substituents selected from alkyl, substituted alkyl, cycloalkyl, substituted cycloalkyl, as well as any of the substituents set forth above.

Presently preferred compounds contemplated by the present invention are those wherein $Ar^1$ and $Ar^2$ are both hydroxyphenyl. When $Ar^1$ and $Ar^2$ are hydroxyphenyl, the ring may bear additional substituents thereon, or may be monosubstituted, e.g., 2-hydroxyphenyl, 3-hydroxyphenyl or 4-hydroxyphenyl.

Additional preferred compounds contemplated by the present invention are those wherein $Ar^1$ and $Ar^2$ are alkoxyphenyl, e.g., methoxyphenyl (e.g., 2-methoxyphenyl, 3-methoxyphenyl or 4-methoxyphenyl).

$R^3$ is an optionally substituted branched alkyl, cycloalkyl, aryl, aralkyl, heteroaryl or heteroarylalkyl moiety, wherein "alkyl", as used herein, refers to straight or branched chain alkyl radicals having in the range of about 1 up to about 12 carbon atoms; "substituted alkyl" refers to alkyl radicals further bearing one or more substituents as set forth above.

As used herein, "cycloalkyl" refers to cyclic ring-containing groups containing in the range of about 3 up to about 12 carbon atoms, and "substituted cycloalkyl" refers to cycloalkyl radicals further bearing one or more substituents selected from alkyl, substituted alkyl, as well as any of the substituents set forth above.

$R^4$, when present, is H or optionally substituted alkyl, aryl, aralkyl, heteroaryl or heteroarylalkyl, wherein alkyl, aryl, aralkyl, heteroaryl and heteroarylalkyl are as defined above, and substituted variations bear one or more of the substituents as set forth above.

$L^1$ and $L^2$ are independently a covalent bond, or a linker having a 1-4 atom backbone, for example, —O—, —S—, —C(O)—, —NR—, —$CH_2$—, —CH=CH—, cyclopropyl, and the like, as well as combinations of any two or more thereof.

A presently preferred linker contemplated for use in the practice of the present invention is —CH=CH—, in either the cis or trans configuration. Thus, presently preferred compounds contemplated by the present invention are those wherein at least one of $L^1$ and $L^2$ is —CH=CH—. Especially preferred compounds according to the invention are those wherein both of $L^1$ and $L^2$ are —CH=CH—. It is presently preferred that both $L^1$ and $L^2$ have a trans configuration.

Embodiments of the invention further include compounds of Formula (I) corresponding to Formula (III):

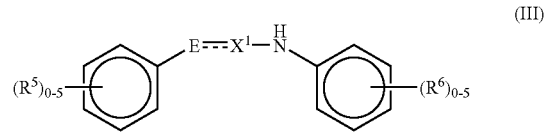

wherein:
E is CH, $CH_2$, or —C(=O);
$X^1$ is N or NH;
each $R^5$ and $R^6$ are independently selected from halogen, hydroxy, alkyl, alkoxy, thiol, thioalkyl, amino, nitro, $SO_2X$, wherein X is H, R, $NH_2$, NHR or $NR_2$; $SO_3Y$, wherein Y is H, $NH_2$, NHR or $NR_2$; C(O)Z, wherein Z is OH, OR, $NH_2$, NHR or $NR_2$; or cyano; and
the dashed line represents an optionally present double bond.

Preferred embodiments of Formula (III) include compounds wherein E is CH, $X^1$ is N, and the bond represent by the dashed line is present; wherein E is $CH_2$, $X^1$ is NH, and the bond represent by the dashed line is absent; and wherein E is —C(=O), $X^1$ is NH, and the bond represent by the dashed line is absent. Additional embodiments of Formula (III) include compounds wherein at least one $R^5$ is $C_1$-$C_3$ alkoxy, such as methoxy; wherein at least one $R^6$ is $C_1$-$C_3$ alkyl, such as when at least two of $R^6$ are methyl.

Figure 13:
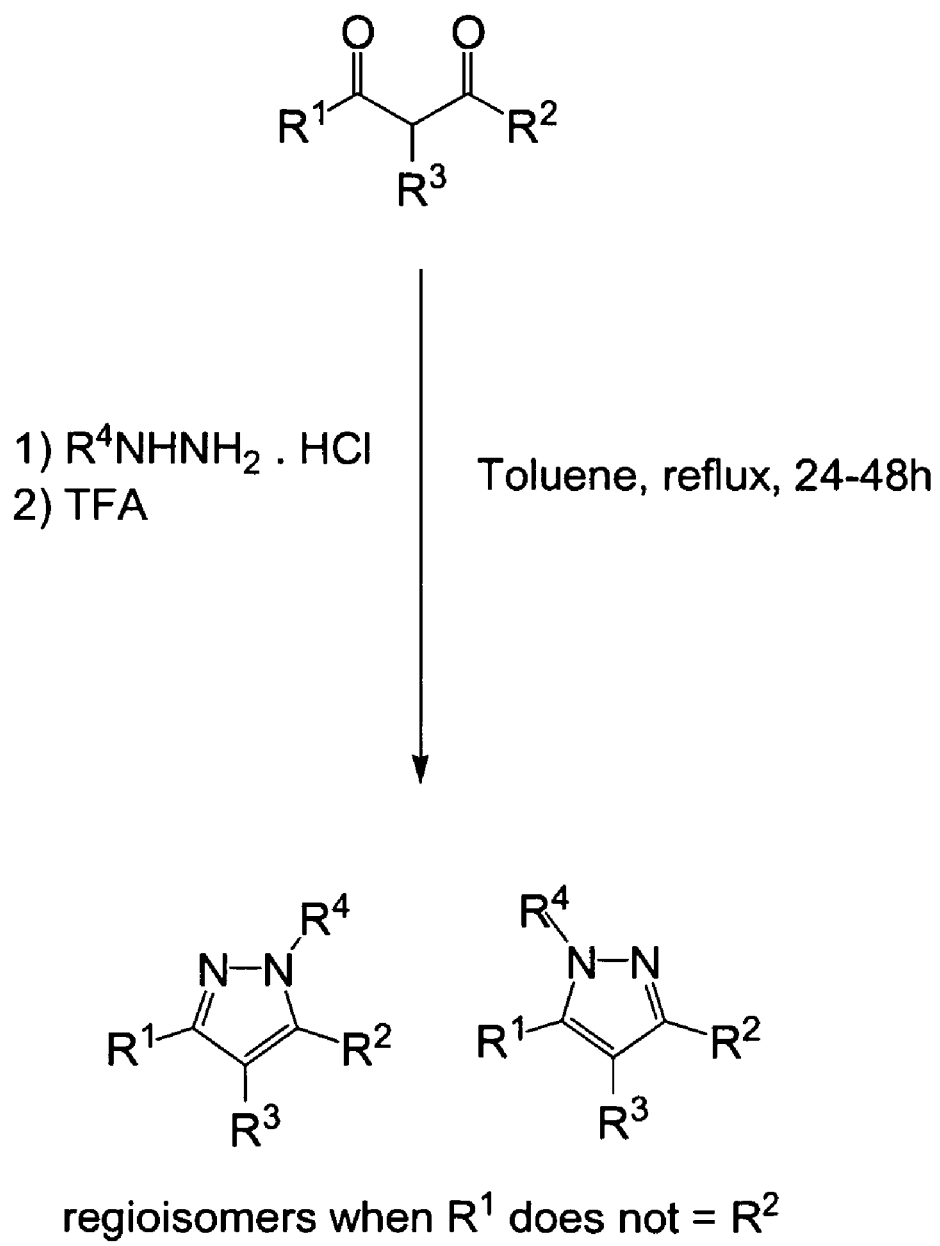
FIG. 13 illustrates a general synthetic scheme useful for the preparation of heteroaromatic invention compounds.
Figure 14:
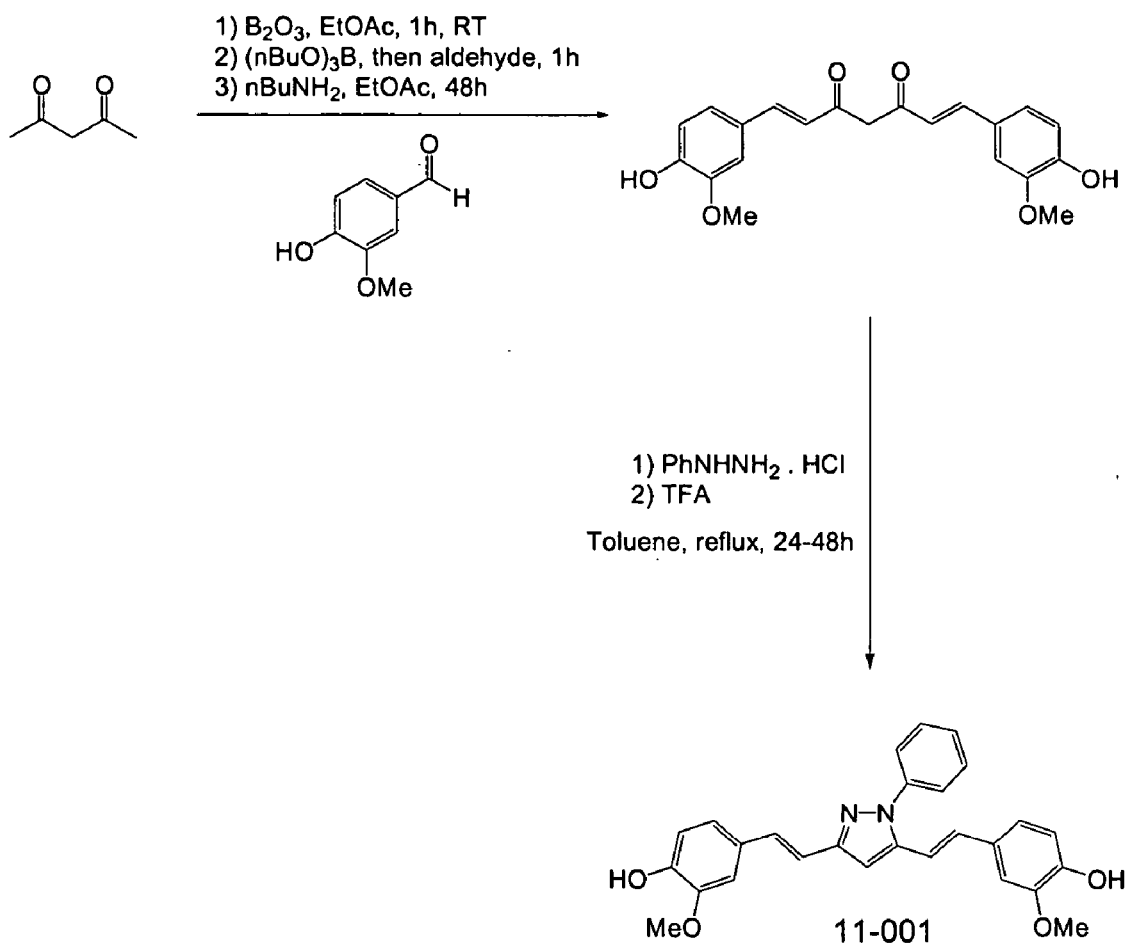
FIG. 14 illustrates a synthetic scheme useful for the preparation of an exemplary pyrazole containing compound according to the present invention.
Figure 15:
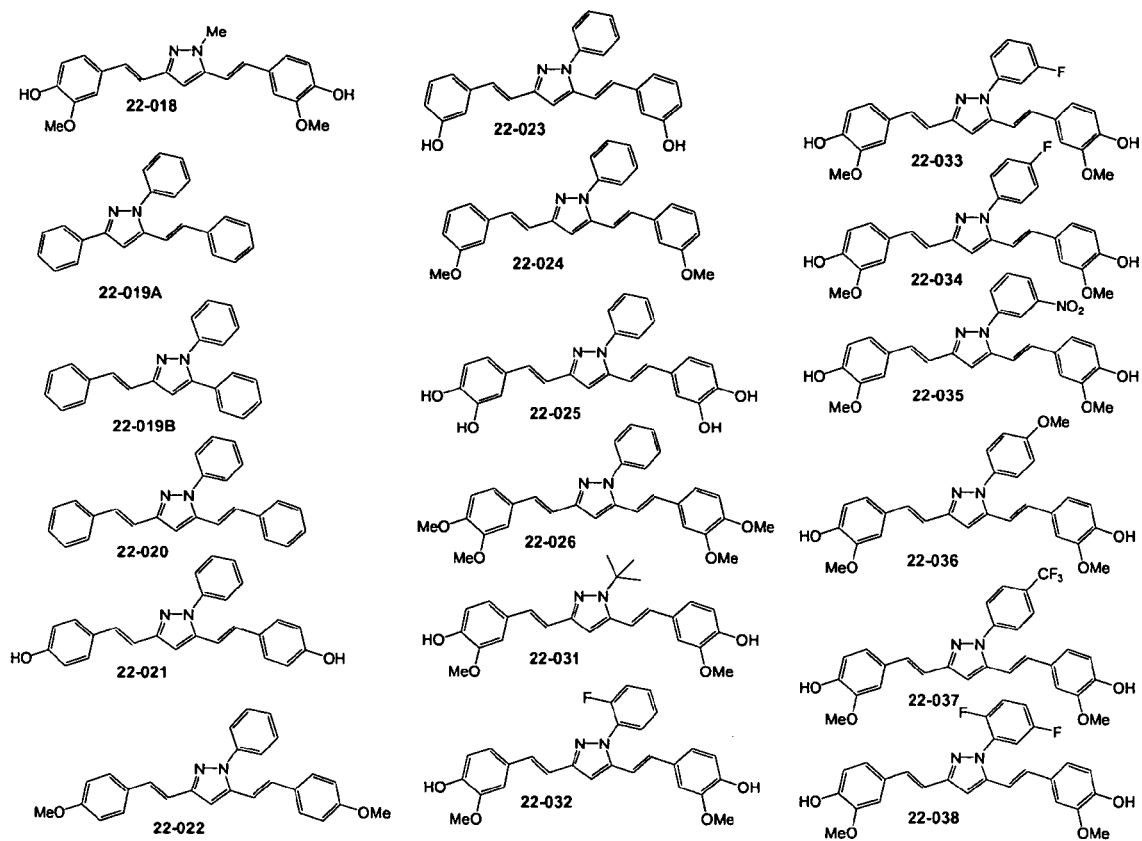
FIG. 15 presents the structures of numerous exemplary compounds according to the present invention.
Figure 16:
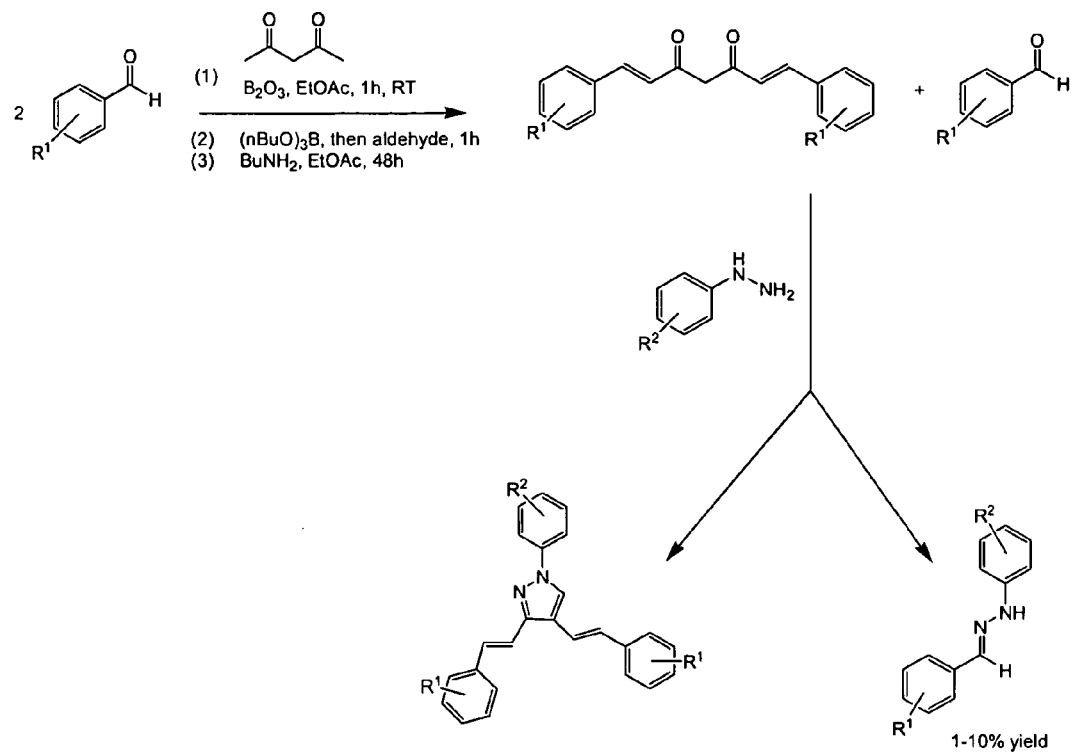
FIG. 16 illustrates a synthetic scheme useful for the preparation of exemplary compounds according to the invention.
Figure 17:
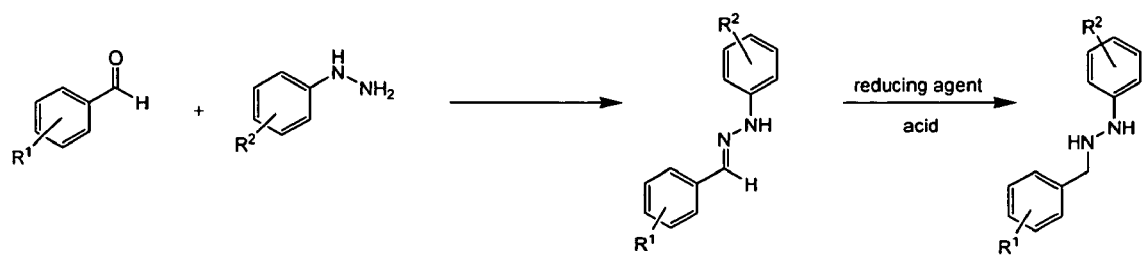
FIG. 17 presents the structures of exemplary compounds according to the invention and a representative synthetic scheme for the preparation of such compounds.
Figure 17:
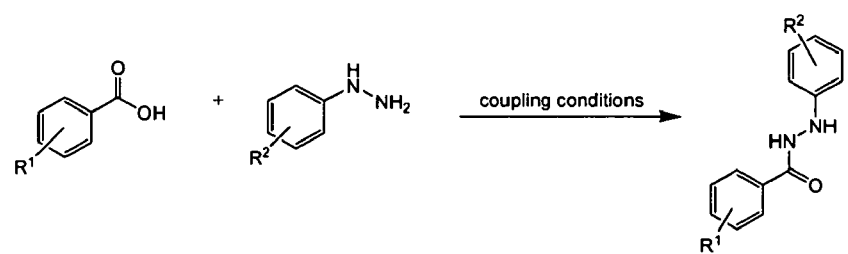
Figure 17:
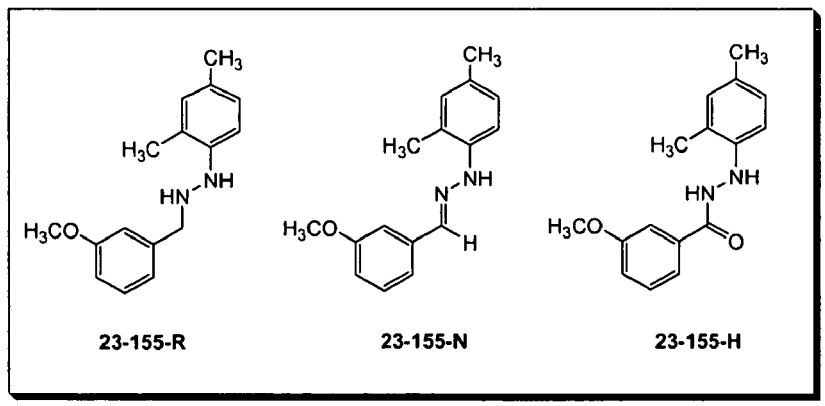

Invention compounds can readily be prepared employing synthetic techniques known in the art. For example, pyrazoles can be prepared from bis-keto compounds as illustrated in FIG. 13. Synthesis of exemplary compounds according to the invention is illustrated in FIGS. 13, 14, 16, and 17. As readily recognized by those of skill in the art, invention compounds having varying core rings can similarly be prepared employing synthetic techniques known in the art.

Invention compounds can optionally be employed in the form of pharmaceutically acceptable salts. Such salts are generally prepared by reacting invention compounds with a suitable organic or inorganic acid or base. Representative organic salts include methanesulfonate, acetate, oxalate, adipate, alginate, aspartate, valerate, oleate, laurate, borate, benzoate, lactate, phosphate, toluenesulfonate (tosylate), citrate, malate, maleate, fumarate, succinate, tartrate, napsylate, methanesulfonate, 2-naphthalenesulfonate, nicotinate, benzenesulfonate, butyrate, camphorate, camphorsulfonate, cyclopentanepropionate, digluconate, dodecylsulfate, glucoheptanoate, glycerophosphate, heptanoate, hexanoate, undecanoate, 2-hydroxyethanesulfonate, ethanesulfonate, and the like. Representative inorganic salts can be formed from inorganic acids such as sulfate, bisulfate, hemisulfate, hydrochloride, chlorate, perchlorate, hydrobromide, hydroiodide, and the like. Examples of a base salt include ammonium salts; alkali metal salts such as sodium salts, potassium salts, and the like; alkaline earth metal salts such as calcium salts, magnesium salts, and the like; salts with organic bases such as dicyclohexylamine salts, N-methyl-D-glucamine, phenylethylamine, and the like; and salts with amino acids such as arginine, lysine, and the like. Such salts can readily be prepared employing methods well known in the art.

In accordance with another embodiment of the present invention, there are provided formulations comprising one or more of the above-described compounds and a pharmaceutically acceptable carrier therefor. Exemplary pharmaceutically acceptable carriers include solids, solutions, emulsions, dispersions, micelles, liposomes, and the like. Optionally, the pharmaceutically acceptable carrier employed herein further comprises an enteric coating.

Pharmaceutically acceptable carriers contemplated for use in the practice of the present invention are those which render invention compounds amenable to oral delivery, sublingual delivery, transdermal delivery, subcutaneous delivery, intracutaneous delivery, intrathecal delivery, intraoccular delivery, rectal delivery, intravenous delivery, intramuscular delivery, topical delivery, nasal delivery, intraperitoneal delivery, vaginal delivery, intracranial delivery, intraventricular delivery, and the like.

Thus, formulations of the present invention can be used in the form of a solid, a solution, an emulsion, a dispersion, a micelle, a liposome, and the like, wherein the resulting formulation contains one or more of the compounds of the present invention, as an active ingredient, in admixture with an organic or inorganic carrier or excipient suitable for enterable or parenteral applications. The active ingredient may be compounded, for example, with the usual non-toxic, pharmaceutically acceptable carriers for tablets, pellets, capsules, suppositories, solutions, emulsions, suspensions and any other suitable for use. The carriers which can be used include glucose, lactose, gum acacia, gelatin, manitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening, and coloring agents and perfumes may be used. The active compound(s) is (are) included in the formulation in an amount sufficient to produce the desired effect upon the process or disease condition.

Invention formulations containing the active ingredient may be in a form suitable for oral use, for example, as tablets, troches, lozenges, aqueous or oily suspensions, dispersible powders or granules, emulsions, hard or soft capsules, or syrups or elixirs. Formulations intended for oral use may be prepared according to any method known to the art for the manufacture of pharmaceutical compositions and such formulations may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients used may be, for example (1) inert diluents such as calcium carbonate, lactose, calcium phosphate or sodium phosphate; (2) granulating and disintegrating agents such corn starch, potato starch or alginic acid; (3) binding agents such as gum tragacanth, corn starch, gelatin or acacia, and (4) lubricating agents such as magnesium stearate, steric acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by such techniques as those described in U.S. Pat. Nos. 4,256,108; 4,160,452; and 4,265,874, to form osmotic therapeutic tablets for controlled release.

In some cases, formulations contemplated for oral use may be in the form of hard gelatin capsules wherein the active ingredient is mixed with inert solid diluent(s), for example, calcium carbonate, calcium phosphate or kaolin. They may also be in the form of soft gelatin capsules wherein the active ingredient is mixed with water or an oil medium, for example, peanut oil, liquid paraffin, or olive oil.

Invention formulations may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids, naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention formulations may also be administered in the form of suppositories for rectal administration of the drug. These formulations may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug. Since individual subjects may present a wide variation in severity of symptoms and each drug has its unique therapeutic characteristics, the precise mode of administration, dosage employed and treatment protocol for each subject is left to the discretion of the practitioner.

The term "effective amount" as applied to invention compounds, means the quantity necessary to effect the desired therapeutic result, for example, a level effective to treat, cure, or alleviate the symptoms of a disease state for which the therapeutic compound is being administered, or to establish homeostasis. Amounts effective for the particular therapeutic goal sought will, of course, depend upon a variety of factors including the disorder being treated, the severity of the disorder, the activity of the specific compound used, the route of administration, the rate of clearance of the specific compound, the duration of treatment, the drugs used in combination or coincident with the specific compound, the age, body weight, sex, diet and general health of the patient, and like factors well known in the medical arts and sciences. These and other general considerations taken into account in determining the "effective amount" are known to those of skill in the art and are described, e.g., in Gilman et al., eds., *Goodman And Gilman's: The Pharmacological Bases of Therapeutics,* 8th ed., Pergamon Press, 1990; and *Remington's Pharmaceutical Sciences,* 17th ed., Mack Publishing Co., Easton, Pa., 1990, each of which is herein incorporated by reference. Effective amounts of invention compounds typically fall in the range of about 0.001 up to 100 mg/kg/day; with levels in the range of about 0.05 up to 10 mg/kg/day being preferred.

In accordance with yet another embodiment of the present invention, there are provided methods for treating a wide variety of neurological indications, e.g., any disease or condition where promoting memory formation is desirable, as well as any disease that is etiologically linked to impaired regulation of neurotrophins or their receptors, inhibition of Bcl-2 or Bcl-$X_L$; inhibition of pro-apoptotic Bcl-2 family members (e.g., Bax and Bad) to prevent unwanted cell death, inhibition of IAP (inhibitor of apoptosis proteins), promotion of IAP binding to caspases, destabilization/blocking of abnormal folding of usually soluble proteins into insoluble, tightly packed shapes, and the like. As used herein, "disease condition" refers to a disorder such as Alzheimer's disease, Parkinson's disease, Huntington's disease, systemic senile amyloidosis, prion disease, scrapie, bovine spongiform encephalopathy, Creutzfeldt-Jakob disease, Gerstmann-Straussler-Scheinker syndrome, type II diabetes, adult onset diabetes, insulinoma, amyotropic lateral sclerosis, amyloid A amyloidosis, AL amyloidosis, familial amyloid polyneuropathy (Portuguese, Japanese and Swedish types), familial transthyretin amyloidosis, familial Mediterranean Fever, familial amyloid nephropathy with urticaria and deafness (Muckle-Wells syndrome), hereditary non-neuropathic systemic amyloidosis (familial amyloid polyneuropathy III), familial amyloidosis of Finnish type, familial amyloid cardiomyopathy (Danish type), isolated cardiac amyloid, isolated atrial amyloidosis, idiopathic (primary) amyloidosis, myeloma or macroglobulinemia-associated amyloidosis, primary localized cutaneous nodular amyloidosis associated with Sjogren's syndrome, reactive (secondary) amyloidosis, hereditary cerebral hemorrhage with amyloidosis of Icelandic type, amyloidosis associated with long term hemodialysis, fibrinogen-associated hereditary renal amyloidosis, amyloidosis associated with medullary carcinoma of the thyroid, lysozyme-associated hereditary systemic amyloidosis, stroke and ischemia, retinal neuropathy, peripheral neuropathy, background neuropathy, and the like.

Thus, in accordance with a particular embodiment of the present invention, there are provided methods for treating acute neural injury, said method comprising administering an effective amount of a compound as described herein to a subject in need thereof.

As readily recognized by those of skill in the art, acute neural injury embraces such injuries as stroke, spinal cord injury, and the like. In such instances, it is recognized by those of skill in the art that nerve cells die as a result of biochemical pathways which include necrosis and various forms of programmed cell death. In addition, glial cells may participate in the cell death. Without wishing to be bound by any theory, the compounds of the invention are believed to be effective, at least in part, by preventing activation of glial cells, and subsequent release of neurotoxic compounds.

As used herein, "treating" refers to inhibiting or arresting the development of a disease, disorder or condition and/or causing the reduction, remission, or regression of a disease, disorder or condition. Those of skill in the art will understand that various methodologies and assays may be used to assess the development of a disease, disorder or condition, and similarly, various methodologies and assays may be used to assess the reduction, remission or regression of a disease, disorder or condition.

As used herein, "administering" refers to providing a therapeutically effective amount of a compound to a subject, using oral, sublingual, intravenous, subcutaneous, transcutaneous, intramuscular, intracutaneous, intrathecal, epidural, intraocular, intracranial, inhalation, rectal, vaginal, and the like administration. Administration in the form of creams, lotions, tablets, capsules, pellets, dispersible powders, granules, suppositories, syrups, elixirs, lozenges, injectable solutions, sterile aqueous or non-aqueous solutions, suspensions or emulsions, patches, and the like, is also contemplated. The active ingredients may be compounded with non-toxic, pharmaceutically acceptable carriers including, glucose, lactose, gum acacia, gelatin, mannitol, starch paste, magnesium trisilicate, talc, corn starch, keratin, colloidal silica, potato starch, urea, dextrans, and the like.

The preferred route of administration will vary with the clinical indication. Some variation in dosage will necessarily occur depending upon the condition of the patient being treated, and the physician will, in any event, determine the appropriate dose for the individual patient. The effective amount of compound per unit dose depends, among other things, on the body weight, physiology, and chosen inoculation regimen. A unit dose of compound refers to the weight of compound employed per administration event without the weight of carrier (when carrier is used).

Targeted-delivery systems, such as polymer matrices, liposomes, and microspheres can increase the effective concentration of a therapeutic agent at the site where the therapeutic agent is needed and decrease undesired effects of the therapeutic agent. With more efficient delivery of a therapeutic agent, systemic concentrations of the agent are reduced because lesser amounts of the therapeutic agent can be administered while accruing the same or better therapeutic results. Methodologies applicable to increased delivery efficiency of therapeutic agents typically focus on attaching a targeting moiety to the therapeutic agent or to a carrier which is subsequently loaded with a therapeutic agent.

Various drug delivery systems have been designed by using carriers such as proteins, peptides, polysaccharides, synthetic polymers, colloidal particles (i.e., liposomes, vesicles or micelles), microemulsions, microspheres and nanoparticles. These carriers, which contain entrapped pharmaceutically useful agents, are intended to achieve controlled cell-specific or tissue-specific drug release.

The compounds described herein can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The compounds described herein, when in liposome form can contain, in addition to the compounds described herein, stabilizers, preservatives, excipients, and the like. The preferred lipids are the phospholipids and the phosphatidyl cholines (lecithins), both natural and synthetic. Methods to form liposomes are known in the art. (See, e.g., Prescott, Ed., Methods in Cell Biology, Volume XIV, Academic Press, New York, N.Y., (1976), p 33 et seq.).

Several delivery approaches can be used to deliver therapeutic agents to the brain by circumventing the blood-brain barrier. Such approaches utilize intrathecal injections, surgical implants (Ommaya, *Cancer Drug Delivery*, 1: 169-178 (1984) and U.S. Pat. No. 5,222,982), interstitial infusion (Bobo et al., *Proc. Natl. Acad. Sci. U.S.A.*, 91: 2076-2080 (1994)), and the like. These strategies deliver an agent to the CNS by direct administration into the cerebrospinal fluid (CSF) or into the brain parenchyma (ECF).

Drug delivery to the central nervous system through the cerebrospinal fluid is achieved, for example, by means of a subdurally implantable device named after its inventor the "Ommaya reservoir". The drug is injected into the device and subsequently released into the cerebrospinal fluid surrounding the brain. It can be directed toward specific areas of exposed brain tissue which then adsorb the drug. This adsorption is limited since the drug does not travel freely. A modified device, whereby the reservoir is implanted in the abdominal cavity and the injected drug is transported by cerebrospinal fluid (taken from and returned to the spine) to the ventricular space of the brain, is used for agent administration. Through omega-3 derivatization, site-specific biomolecular complexes can overcome the limited adsorption and movement of therapeutic agents through brain tissue.

Another strategy to improve agent delivery to the CNS is by increasing the agent absorption (adsorption and transport) through the blood-brain barrier and the uptake of therapeutic agent by the cells (Broadwell, *Acta Neuropathol.*, 79: 117-128 (1989); Pardridge et al., *J. Pharmacol. Experim. Therapeutics*, 255: 893-899 (1990); Banks et al., *Progress in Brain Research*, 91:139-148 (1992); Pardridge, *Fuel Homeostasis and the Nervous System*, ed.: Vranic et al., Plenum Press, New York, 43-53 (1991)). The passage of agents through the blood-brain barrier to the brain can be enhanced by improving either the permeability of the agent itself or by altering the characteristics of the blood-brain barrier. Thus, the passage of the agent can be facilitated by increasing its lipid solubility through chemical modification, and/or by its coupling to a cationic carrier, or by its covalent coupling to a peptide vector capable of transporting the agent through the blood-brain barrier. Peptide transport vectors are also known as blood-brain barrier permeabilizer compounds (U.S. Pat. No. 5,268,164). Site specific macromolecules with lipophilic characteristics useful for delivery to the brain are described in U.S. Pat. No. 6,005,004.

Other examples (U.S. Pat. Nos. 4,701,521, and 4,847,240) describe a method of covalently bonding an agent to a cationic macromolecular carrier which enters into the cells at relatively higher rates. These patents teach enhancement in cellular uptake of bio-molecules into the cells when covalently bonded to cationic resins.

U.S. Pat. No. 4,046,722 discloses anti-cancer drugs covalently bonded to cationic polymers for the purpose of directing them to cells bearing specific antigens. The polymeric carriers have molecular weights of about 5,000 to 500,000. Such polymeric carriers can be employed to deliver compounds described herein in a targeted manner.

Further work involving covalent bonding of an agent to a cationic polymer through an acid-sensitive intermediate (also known as a spacer) molecule, is described in U.S. Pat. Nos. 4,631,190 and 5,144,011. Various spacer molecules, such as cis-aconitic acid, are covalently linked to the agent and to the polymeric carrier. They control the release of the agent from the macromolecular carrier when subjected to a mild increase in acidity, such as probably occurs within a lysosome of the cell. The drug can be selectively hydrolyzed from the molecular conjugate and released in the cell in its unmodified and active form. Molecular conjugates are transported to lysosomes, where they are metabolized under the action of lysosomal enzymes at a substantially more acidic pH than other compartments or fluids within a cell or body. The pH of a lysosome is shown to be about 4.8, while during the initial stage of the conjugate digestion, the pH is possibly as low as 3.8.

In accordance with still another embodiment of the present invention, there are provided methods for treating chronic neurodegenerative disease, said method comprising administering an effective amount of a compound as described herein to a subject in need thereof.

As readily recognized by those of skill in the art, chronic neurodegenerative disease embraces such indications as Alzheimer's disease, Parkinson's disease, Huntington's disease, amyotrophic lateral sclerosis, glaucoma, retinal degeneration, macular degeneration, age-related hearing loss, mild cognitive impairment, dementia (including, for example, frontotemporal dementia, AIDS dementia, and the like), progressive supranuclear palsy, spinocerebellar ataxias, and the like.

In accordance with a further embodiment of the present invention, there are provided methods of protecting neurons in a subject in need thereof, said method comprising administering an effective amount of a compound as described herein to said subject. As used herein, the phrase "protecting neurons" refers to preventing nerve damage, deterioration of neurons, and/or death of neurons, no matter what the cause or causative agent. Throughout neuronal life, neurons are subjected to various factors that affect and contribute to the natural aging process, which may result in deterioration of neuronal physiology, morphology, and the like. Neurons are also subject to various factors that cause injury and damage, resulting in reduction or loss of some or all physiological and morphological characteristics. Factors can be endogenous (e.g., neurotropins, vitamins, and the like; or released following stroke or other injury) or exogenous factors such as alcohol, pharmaceutical agents, and the like.

In accordance with a still further embodiment of the present invention, there are provided methods for promoting neuroregeneration in a subject in need thereof, said method comprising administering an effective amount of a compound as described herein to said subject. As used herein, "neuroregeneration" refers to regrowth of neuron projections to repair damage thereto (where the cell body remains intact) and the sprouting of new projections. Neuroregeneration may be needed in a subject when neuropathies are present. Exemplary neuropathies include retinal neuropathy, peripheral neuropathy, background neuropathy, and the like.

In accordance with yet another embodiment of the present invention, there are provided methods for promoting memory formation, said method comprising administering an effective amount of a compound as described herein to a subject in need thereof.

The invention will now be described in greater detail by reference to the following non-limiting examples.

EXAMPLE 1

Assays for Detecting Neuroprotective Activity

Primary cortical neurons are prepared from 18-day-old embryos of Sprague-Dawley rats as described (Liu and Schubert J. Neurochem. 69, 2285-2293 (1997) and J. Neurochem. 71, 2322-2329 (1998)). Briefly, the cerebral cortex is dissected out under an anatomical microscope and is freed of meninges and blood vessels. The cortex is cut into small pieces and is then dissociated by trypsin digestion and passed through a pipette tip. Dissociated neurons are suspended in various media and plated on polylysine-coated 35 mm tissue culture dishes ($1\times10^6$ cells/dish). Several different culture conditions were used. Invention compounds were added to cell culture dishes. Cell survival was measure 2-7 days after compound administration.

The following serum-containing medium was used: minimal essential medium (Sigma) containing 30 mM glucose, 2 mM glutamine, 1 mM pyruvate, penicillin (100 U/ml), streptomycin (100 μg/ml), and 10% fetal calf serum. At a plating density of $1\times10^6$ cells/dish, most neurons die after one week of culture in this medium. If plated at a density of $2\times10^6$ cells/dish, then most neurons survive. Glia proliferate in this medium regardless of the initial cell density. Therefore the cell density-dependent neuronal survival in this system is most likely dependent on the neurotrophic factors secreted by the neurons, not by the glia. The results are the same when glial proliferation is inhibited by cytosine arabinoside.

A serum-free medium containing DMEM/F-12 plus N2 supplements (Invitrogen). When plated at a density of $1\times10^6$ cells/dish, almost all neurons die within three days. The cell death mechanisms in this culture medium are most likely to be oxidative stress and trophic factor deficiency.

EXAMPLE 2

Structure-Activity Relationship of a Series of Compounds of Structure I

A number of compounds according to the present invention were synthesized (using standard synthetic techniques) to explore the structure-activity relationships. The structures of exemplary invention compounds tested are provided herein. The structure-activity relationships of various compounds according to the present invention with rat primary cortical neurons cultured in serum-containing or serum-free medium are set forth in Table 1.

TABLE 1

Structure-activity relationship I: rat primary cortical neurons cultured in serum- containing or serum-free medium.

| Compound | Neuroprotective activity at 1 μM |
|---|---|
| 11-001 | +++ |
| 11-002 | 0 |
| 11-006 | 0 |
| 11-016 | 0 |

TABLE 1-continued

Structure-activity relationship I: rat primary cortical neurons cultured in serum- containing or serum-free medium.

| Compound | Neuroprotective activity at 1 μM |
|---|---|
| 11-021 | 0 |
| 22-017 | 0 |
| 22-018 | + |
| 22-019 | +++ |
| 22-020 | 0 |
| 22-021 | ++++ |
| 22-022 | 0 |
| 22-023 | ++++ |
| 22-024 | 0 |
| 22-025 | ++ |
| 22-026 | 0 |
| 22-031 | +++ |
| 22-032 | ++ |
| 22-033 | + |
| 22-034 | + |
| 22-035 | ++ |
| 22-036 | ++ |
| 22-037 | +++ |
| 22-038 | +++ |
| 22-043A | 0 |
| 22-043B | 0 |
| 23-155 | ++++ |

Compounds according to the present invention show clear, specific structure-activity relationships. For example, changes of just one —OH group or —OCH$_3$ group or a different position of just one —OH group or —OCH$_3$ group has the potential to greatly affect activity, indicating the presence of a specific target for these compounds.

The structure-activity relationships of various compounds according to the present invention was also determined by measuring excitotoxicity in mouse primary cortical neurons, as follows:

Excitotoxicity assay was done with primary cultures of cortical neurons prepared from embryonic day 14 BALB/c mouse embryo cortices as described (Schubert and Piasecki, J. Neurosci. 21, 7455-7462 (2001)). The cells were plated at $1\times10^5$ cell/well in 96-well ploy-L-lysine and laminin-coated microtiter plates. Cortical neurons after 11 days of culture were exposed to 10 μM glutamate for 10 min, followed by the addition of varying concentrations of invention compounds. Cell viability was determined 24 hr later with the 3-(4,5-dimethylthiazol-2-yl)-2,5-diphenyltetrazolium bromide (MTT) assay. MTT reduction is a widely used method for measuring cell proliferation and viability (Mosmann, J. Immunol. Methods 65:55-63 (1983)). Results are set forth in Table 2.

TABLE 2

Structure-activity relationship II: excitotoxicity in mouse primary cortical neurons

| Compound | Neuroprotective activity at 10 μM |
|---|---|
| 11-001 | ++ |
| 22-019 | ++ |
| 22-020 | + |
| 22-021 | +++ |
| 22-022 | ++ |
| 22-023 | ++++ |
| 22-024 | ++ |
| 22-025 | + |
| 22-026 | + |
| 22-43B | ++ |

Similar excitotoxicity assays as described above were also conducted with invention compounds using HT22 cells. After exposure with 1 mM, 2 mM, 2.5 mM, or 5 mM glutamate, cell viability was determined with the MTT assay. Compound 23-155 exhibited an EC50 of ≈70 nM following 5 mM glutamate exposure, and an EC50 of ≈30 nM following 2 mM glutamate exposure in these assays. Furthermore, compound 23-155 at concentrations ranging from 0.1-1.0 µM imparted greater than 75% MTT reduction after glutamate exposure at all tested concentrations.

Essentially identical structure-activity relationships were found with these two assays. Compounds according to the present invention were also found to protect against excitotoxicity in mouse primary cortical neurons, although concentrations of higher than 5 µM were required. The structure-activity relationship of invention compounds against excitotoxicity is similar, but not identical, to that shown in Table 1.

EXAMPLE 3

Pharmacokinetic Evaluation of Invention Compounds

The present example demonstrates the ability of compounds of the invention to cross the blood brain barrier in mice. The pharmacokinetic properties of compound 11-001 (see FIG. 14) after a single oral dose were studied in 10-week old female BALB/c mice. Compound 11-001 was emulsified in 2.5% carboxymethyl cellulose at a concentration of 20 mg/ml and administered by gavage at a dosage of 400 mg/kg body weight (administered volume was 20 ml/kg body weight). The mice were then sacrificed at various intervals after administration (0, 1 hr, 2 hr, 4 hr, and 6 hr). Plasma was obtained from blood (mixed with $K_3$EDTA to prevent coagulation) by centrifugation at 4,300 g for 10 min, extracted twice with ethyl acetate/propanol (9:1, v/v). The extracts were centrifuged at 5,000 g for 10 min to form aqueous/organic layers. The organic layer containing compound 11-001 was centrifuged at 20,000 g for 10 min to sediment particles. The extraction recovery from plasma was approximately 90%. Thirty µl thereof were analyzed by HPLC equipped with a C18 reversed phase column and compound 11-001 was detected at 330 nm. The elution solvent system was 50% acetonitrile, 50% water and 1 g/L trifluoroacetic acid with a flow rate of 1 ml/min.

To study the distribution of compound 11-001 in brain at various time intervals (0, 1 hr, 2 hr, 4 hr, and 6 hr) after gavage (400 mg/kg), the mice were anesthetized with cloral hydrate and perfused through the heart with phosphate buffered saline (PBS) to remove blood in the brain. The mice were then decapitated, the brains removed, and quickly frozen and stored at −80° C. before further analysis. To measure the level of compound 11-001 in the brain, weighed brain pieces were homogenized by sonication in 3 volumes of PBS. The homogenates were then extracted and measured by HPLC as described above. The results are shown in Table 3.

TABLE 3

Plasma concentration and brain content of compound 11-001 after a single oral dose (400 mg/kg) of 11-001 by gavage

| Time after gavage | Plasma 11-001 concentration (µg/ml) | Brain 11-001 content (µg/g brain) |
| --- | --- | --- |
| 0 hr | 0 | 0 |
| 1 hr | 1.84 | 2.62 |
| 2 hr | 2.30 | 1.28 |

TABLE 3-continued

Plasma concentration and brain content of compound 11-001 after a single oral dose (400 mg/kg) of 11-001 by gavage

| Time after gavage | Plasma 11-001 concentration (µg/ml) | Brain 11-001 content (µg/g brain) |
| --- | --- | --- |
| 4 hr | 1.25 | 0.89 |
| 6 hr | 0.67 | 0.95 |

This study shows that compound 11-001 is rapidly absorbed into blood and quickly distributed to the brain. The maximum plasma concentration was reached around 2 hr after administration while maximum brain concentration was reached 1 hr after gavage. Six hr after administration, the majority of compound 11-001 in blood and in brain have been eliminated. Thus, these results do show that compound 11-001 can be orally absorbed and traverse the blood-brain barrier.

EXAMPLE 4

Invention Compounds Alter CREB Phosphorylation

The present example demonstrates the ability of invention compounds to alter activity of a kinase or a phosphatase which is involved in phosphorylation of the neuroprotective transcription factor, cyclic-AMP binding protein (CREB). CREB activation has been linked to cell survival and accordingly, is considered to be a validated therapeutic target (Vaishnov, et al, 2003). Similar to the concept of programmed cell death which involves transcription factors pivotal in switching on the nerve cell death program is the transcriptional control of programmed cell life. For example, recent studies of the activation of the CREB transcription factor in stroke models have shown that CREB is phosphorylated (and presumably activated) in neurons that survive this insult. Further studies show that the CREB survival pathway may be inactivated by neurotoxins and genes involved in neurodegenerative disorders.

Figure 18:
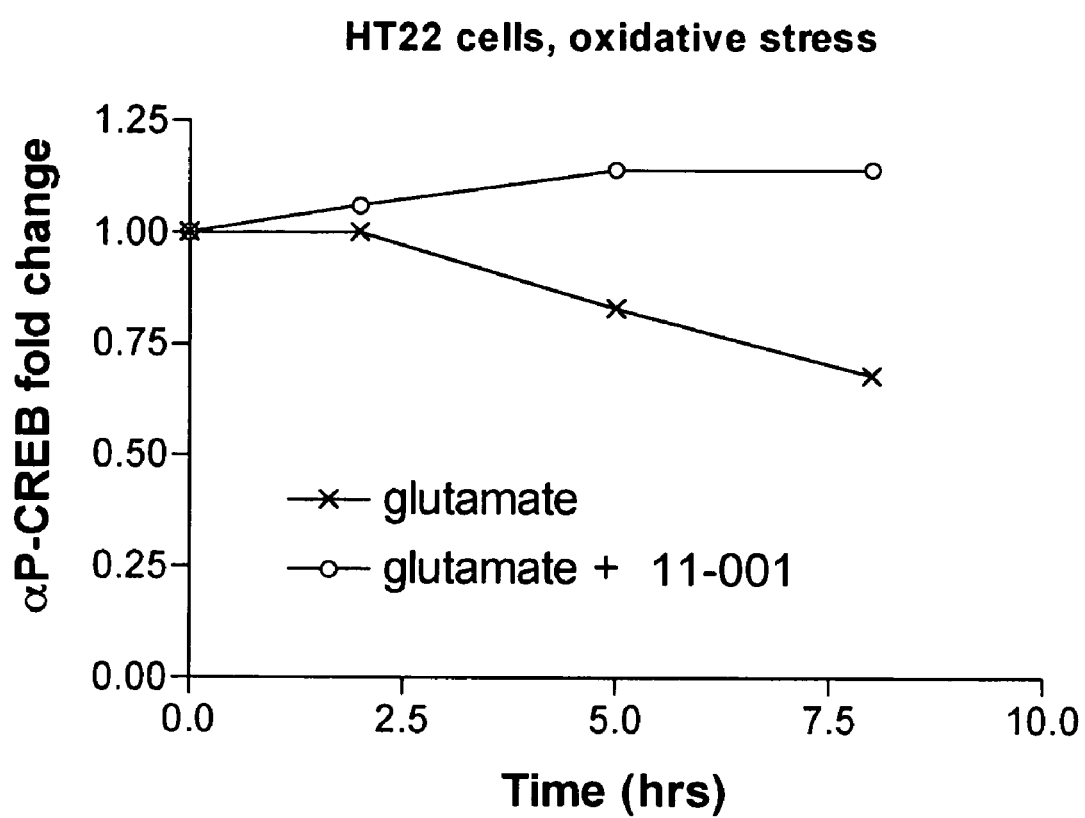
FIG. 18 provides a graph depicting the effect of an exemplary invention compound on CREB phosphorylation in HT22 cells in response to oxidative stress.

CREB phosphorylation in response to oxidative stress was evaluated in the presence of invention compounds. Glutamate was added to HT22 cells in the presence or absence of compound 11-001 (at 1 µM). As illustrated in FIG. 18, the ratio of phosphorylated CREB to total CREB was measured as a function of time. Furthermore, all of the HT22 cells died in the absence of compound 11-001, and over 90% lived in the presence of compound 11-001.

A panel of 14 protein kinases was screened against compound 11-001. Compound 11-001 partially inhibited the nerve-specific isoform of JNK and JNK-3 kinases. None of the other enzymes that were assayed, including JNK-1 or JNK-2, were affected. In HT22 cells and primary cortical neurons, compound 11-001 blocked p38 and JNK phosphorylation caused by glutamate by about 30%, and inhibited cell death. The phosphorylation of the other tested kinases was not altered.

EXAMPLE 5

Neuroprotective Effects of Invention Compounds Against Oxidative Stress

The present example demonstrates the protective effects imparted by invention compounds against glutamate induced oxidative stress. See Tan et al. 2002 for further information regarding signaling pathways used to kill and protect HT22 cells from oxidative stress-induced cell death.

Figure 19:
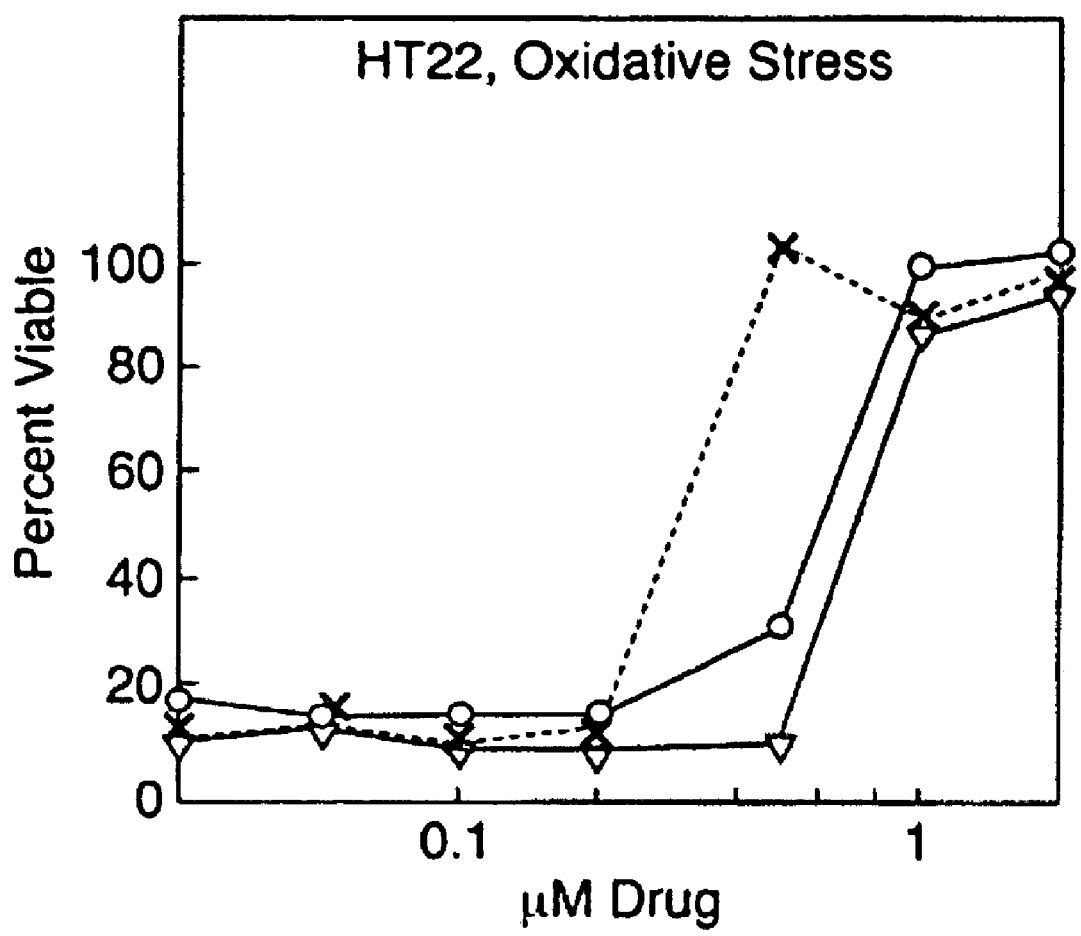
FIG. 19 provides a graph illustrating the neuroprotective effect of exemplary invention compounds on cell viability in response to oxidative stress in HT22 cells.

HT22 hippocampal neurons were treated with 5 mM glutamate and increasing concentrations of invention compounds. Cell viability was measured 24 hr later by the MTT assay (Davis and Maher, 1994). FIG. 19 presents a graph illustrating cell viability at tested concentrations of compound 11-001 and derivatives thereof. In this assay, compound 23-155 exhibited an EC50 of ≈50 nM, which was approximately five to ten times more effective than compound 11-001.

EXAMPLE 6

Effects of Invention Compounds on Enzymes Involved in Memory Formation

The present example demonstrates the ability of invention compounds to activate CaM Kinase II, a key enzyme involved in memory formation.

Figure 20:
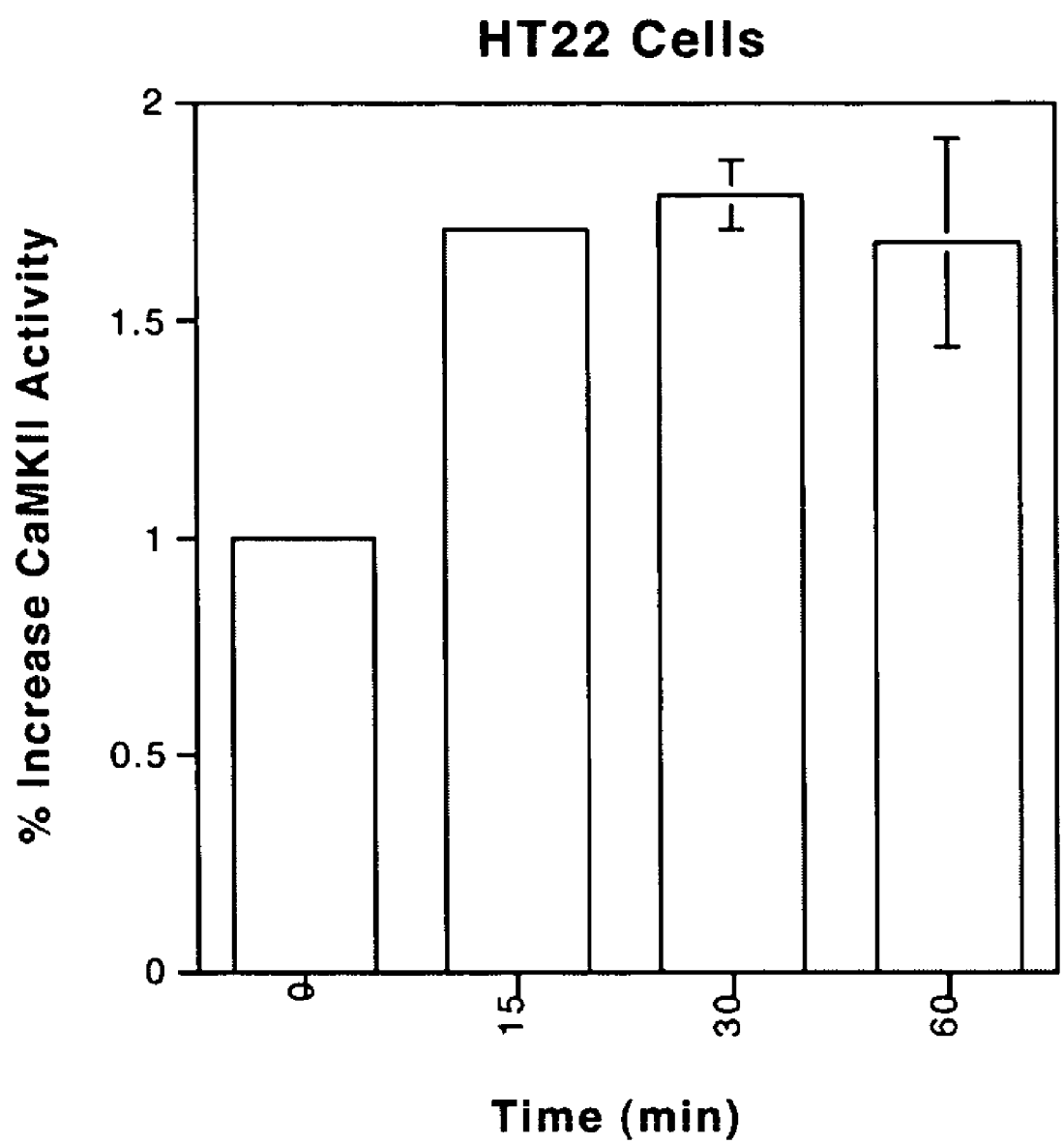
FIG. 20 summarizes the effect of invention compounds on CaM Kinase II activity. HT22 cells were treated with 2 µM of an exemplary invention compound for the indicated times. Cell extracts were prepared and assayed for CaMKII activity using a kit from Upstate Biotechnology. Similar results were obtained in 2 independent experiments.

HT22 hippocampal neurons were treated with 2 μM of an exemplary invention compound for the indicated times. Cell extracts were prepared and assayed for CaMKII activity using a kit from Upstate Biotechnology. FIG. 20 summarizes the effect of invention compounds on CaM Kinase II activity. Similar results were obtained in 2 independent experiments.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

What is claimed is:

1. A compound comprising the structure corresponding to Formula (II):

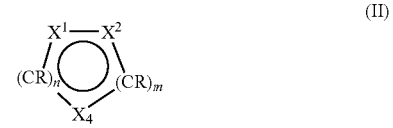

wherein:
m is 1,
n is 1,
$X^1$ is N or $NR^3$,
$X^2$ is N or $NR^3$,
$X^4$ is CH,
one R is $-L^1-Ar^1$,
one R is $-L^2-Ar^2$,
$L^1$ and $L^2$ are —CH=CH—,
$Ar^1$ and $Ar^2$ are independently selected from the group consisting of phenyl, 4-hydroxyphenyl, 3-hydroxyphenyl, 3,4-dihydroxyphenyl and 3-methoxy, 4-hydroxy phenyl, and
$R^3$ is selected from the group consisting of phenyl, isobutyl, 2-fluorophenyl, 3-fluorophenyl, 4-fluorophenyl, 3-nitrophenyl, 4-methoxyphenyl, 4-trifluoromethylphenyl, and 2,5-difluorophenyl.

2. The compound of claim 1 wherein both $L^1$ and $L^2$ have a trans configuration.

3. The compound of claim 1 wherein $Ar^1$ and $Ar^2$ are hydroxyphenyl.

4. The compound of claim 3 wherein said hydroxyphenyl is 2-hydroxyphenyl, 3-hydroxyphenyl or 4-hydroxyphenyl.

5. A composition comprising a compound according to claim 1 and a pharmaceutically acceptable carder therefor.

6. The composition of claim 5 wherein said pharmaceutically acceptable carrier is suitable for oral administration.

7. The compound of claim 1 wherein each of $Ar^1$ and $Ar^2$ are hydroxy, alkoxy-substituted phenyl.

8. The compound of claim 7 wherein each of $Ar^1$ and $Ar^2$ are 3-methoxy, 4-hydroxyphenyl.

9. The compound of claim 1 wherein:
$X^1$ is $NR^3$,
$X^2$ is N,
$R^3$ is phenyl,
$L^1$ and $L^2$ are each a linker having the structure —CH=CH—, and
$Ar^1$ and $Ar^2$ are each 3-methoxy, 4-hydroxy phenyl.

10. The compound of claim 1 wherein:
$X^1$ is $NR^3$,
$X^2$ is N,
$R^3$ is phenyl,
$L^1$ and $L^2$ are each a linker having the structure —CH=CH—, and
$Ar^1$ and $Ar^2$ are each phenyl.

11. The compound of claim 1 wherein:
$X^1$ is $NR^3$,
$X^2$ is N,
$R^3$ is phenyl,
$L^1$ and $L^2$ are each a linker having the structure —CH=CH—, and
$Ar^1$ and $Ar^2$ are each 4-hydroxy phenyl.

12. The compound of claim 1 wherein:
$X^1$ is $NR^3$,
$X^2$ is N,
$R^3$ is phenyl,
$L^1$ and $L^2$ are each a linker having the structure —CH=CH—, and
$Ar^1$ and $Ar^2$ are each 3-hydroxy phenyl.

13. The compound of claim 1 wherein:
$X^1$ is $NR^3$,
$X^2$ is N,
$R^3$ is phenyl,
$L^1$ and $L^2$ are each a linker having the structure —CH=CH—, and
$Ar^1$ and $Ar^2$ are each 3,4-dihydroxy phenyl.

14. The compound of claim 1 wherein:
$X^1$ is $NR^3$,
$X^2$ is N,
$R^3$ is t-butyl,
$L^1$ and $L^2$ are each a linker having the structure —CH=CH—, and
$Ar^1$ and $Ar^2$ are each 3-methoxy, 4-hydroxy phenyl.

15. The compound of claim 1 wherein:
$X^1$ is $NR^3$,
$X^2$ is N,
$R^3$ is 2fluorophenyl,
$L^1$ and $L^2$ are each a linker having the structure —CH=CH—, and
$Ar^1$ and $Ar^2$ are each 3-methoxy, 4-hydroxy phenyl.

16. The compound of claim 1 wherein:
$X^1$ is $NR^3$,
$X^2$ is N,
$R^3$ is 3-fluorophenyl,
$L^1$ and $L^2$ are each a linker having the structure —CH=CH—, and
$Ar^1$ and $Ar^2$ are each 3-methoxy, 4-hydroxy phenyl.

17. The compound of claim 1 wherein:
$X^1$ is $NR^3$,
$X^2$ is N,
$R^3$ is 4-fluorophenyl,
$L^1$ and $L^2$ are each a linker having the structure —CH=CH—, and
$Ar^1$ and $Ar^2$ are each 3-methoxy, 4-hydroxy substituted phenyl.

18. The compound of claim 1 wherein:
$X^1$ is $NR^3$,
$X^2$ is N,
$R^3$ is 3-nitrophenyl,
$L^1$ and $L^2$ are each a linker having the structure —CH=CH—, and
$Ar^1$ and $Ar^2$ are each 3-methoxy, 4-hydroxy substituted phenyl.

19. The compound of claim 1 wherein:
$X^1$ is $NR^3$,
$X^2$ is N,
$R^3$ is 4-methoxyphenyl,
$L^1$ and $L^2$ are each a linker having the structure —CH=CH—, and
$Ar^1$ and $Ar^2$ are each 3-methoxy, 4-hydroxy substituted phenyl.

20. The compound of claim 1 wherein:
$X^1$ is $NR^3$,
$X^2$ is N,
$R^3$ is 4-trifluoromethylphenyl,
$L^1$ and $L^2$ are each a linker having the structure —CH=CH—, and
$Ar^1$ and $Ar^2$ are each 3-methoxy, 4-hydroxy substituted phenyl.

21. The compound of claim 1 wherein:
$X^1$ is $NR^3$,
$X^2$ is N,
$R^3$ is 2,5-difluorophenyl,
$L^1$ and $L^2$ are each a linker having the structure —CH=CH—, and
$Ar^1$ and $Ar^2$ are each 3-methoxy, 4-hydroxy substituted phenyl.

* * * * *